US00RE49445E

(19) United States
(12) Reissued Patent
Brown et al.

(10) Patent Number: US RE49,445 E
(45) Date of Reissued Patent: Mar. 7, 2023

(54) N-(CYANOMETHYL)-4-(2-(4-MORPHOLINOPHENYLAMINO) PYRIMIDIN-4-YL)BENZAMIDE

(71) Applicant: SIERRA ONCOLOGY, INC., Plymouth, MI (US)

(72) Inventors: Brandon H. Brown, Burlingame, CA (US); Ernest A. Carra, Foster City, CA (US); Jeffrey N. Hemenway, San Mateo, CA (US); Henry Morrison, Dublin, CA (US); Troy Reynolds, San Francisco, CA (US); Bing Shi, Redwood City, CA (US); Dimitrios Stefanidis, Mountain View, CA (US); Fang Wang, Foster City, CA (US); Matthew Robert Warr, Madison, CT (US); James Andrew Whitney, Guilford, CT (US); Yan Xin, San Carlos, CA (US)

(73) Assignee: Sierra Oncology, Inc., Plymouth, MI (US)

(21) Appl. No.: 17/013,342

(22) Filed: Sep. 4, 2020

Related U.S. Patent Documents

Reissue of:
(64) Patent No.: 9,469,613
Issued: Oct. 18, 2016
Appl. No.: 14/736,690
Filed: Jun. 11, 2015

U.S. Applications:
(63) Continuation of application No. 16/164,681, filed on Oct. 18, 2018, now Pat. No. Re. 48,285, which is an application for the reissue of Pat. No. 9,469,613.
(Continued)

(51) Int. Cl.
*C07D 239/42* (2006.01)
*A61K 31/535* (2006.01)
(Continued)

(52) U.S. Cl.
CPC ..... *C07D 239/42* (2013.01); *A61K 31/535* (2013.01); *A61K 31/5377* (2013.01); *C07D 265/30* (2013.01); *C07B 2200/13* (2013.01)

(58) Field of Classification Search
CPC .. C07D 239/42; C07D 265/30; C07D 413/12; A61K 31/535; A61K 31/5377;
(Continued)

(56) References Cited

U.S. PATENT DOCUMENTS 3,481,932 A 12/1969 Wagner
4,943,593 A 7/1990 Palfreyman et al.
(Continued)

FOREIGN PATENT DOCUMENTS

AU 2007209928 A1 8/2007
AU 2008226327 B2 12/2012
(Continued)

OTHER PUBLICATIONS

Fisher et al., "An investigation into structural changes due to Deuteration," 2008, Acta Cryst., A64, pp. 359-367 (9 pages).
(Continued)

*Primary Examiner* — Jerry D Johnson
*Assistant Examiner* — Alan Diamond
(74) *Attorney, Agent, or Firm* — Fish & Richardson P.C.

(57) ABSTRACT

The present invention relates to stable novel salt forms of N-(cyanomethyl)-4-(2-(4-morpholinophenylamino)pyrimidin-4-yl)benzamide that are suitable for the preparation of pharmaceutical formulations thereof, and their therapeutic use.

39 Claims, 14 Drawing Sheets

Related U.S. Application Data

(60) Provisional application No. 62/011,315, filed on Jun. 12, 2014.

(51) Int. Cl.
*A61K 31/5377* (2006.01)
*C07D 265/30* (2006.01)

(58) Field of Classification Search
CPC ..... C07B 2200/13; A61P 7/00; A61P 35/00; A61P 35/02; A61P 43/00
See application file for complete search history.

(56) References Cited

U.S. PATENT DOCUMENTS

| | | | | |
|---|---|---|---|---|
| 4,965,288 | A | 10/1990 | Palfreyman et al. | |
| 4,997,854 | A | 3/1991 | Kagan et al. | |
| 5,021,456 | A | 6/1991 | Palfreyman et al. | |
| 5,059,714 | A | 10/1991 | Palfreyman et al. | |
| 5,120,764 | A | 6/1992 | McCarthy et al. | |
| 5,182,297 | A | 1/1993 | Palfreyman et al. | |
| 5,252,608 | A | 10/1993 | Palfreyman et al. | |
| 6,600,037 | B1 | 7/2003 | Davis et al. | |
| 7,235,588 | B2 | 6/2007 | Siddiqui et al. | |
| 7,593,820 | B2 | 9/2009 | Wilks et al. | |
| 8,486,941 | B2 * | 7/2013 | Burns | C07D 239/42 514/235.8 |
| 8,809,359 | B2 | 8/2014 | Burns | |
| 9,469,613 | B2 | 10/2016 | Brown et al. | |
| 9,518,027 | B2 | 12/2016 | Silverman | |
| 9,604,935 | B2 | 3/2017 | Lv et al. | |
| 9,776,973 | B2 | 10/2017 | Silverman | |
| 9,809,559 | B2 | 11/2017 | Brown et al. | |
| RE48,285 | E * | 10/2020 | Brown | A61K 31/5377 |
| 2002/0147339 | A1 | 10/2002 | Batchelor et al. | |
| 2003/0087922 | A1 | 5/2003 | Bethiel et al. | |
| 2004/0180914 | A1 | 9/2004 | Batchelor et al. | |
| 2004/0248871 | A1 | 12/2004 | Farjanel et al. | |
| 2006/0079543 | A1 | 4/2006 | Sum et al. | |
| 2010/0069417 | A1 | 3/2010 | Bouaboula et al. | |
| 2010/0197671 | A1 | 8/2010 | Burns et al. | |
| 2010/0310531 | A1 | 12/2010 | Wagner et al. | |
| 2011/0218704 | A1 * | 9/2011 | Kanekawa | B62D 5/049 701/29.2 |
| 2014/0005161 | A1 | 1/2014 | Burns | |
| 2014/0005180 | A1 | 1/2014 | Burns et al. | |
| 2014/0011803 | A1 | 1/2014 | Burns et al. | |
| 2014/0073643 | A1 | 3/2014 | Smith et al. | |
| 2014/0171433 | A1 | 6/2014 | Burns et al. | |

FOREIGN PATENT DOCUMENTS

| | | | |
|---|---|---|---|
| AU | 2013201306 | A1 | 3/2013 |
| AU | 2016200866 | A1 | 2/2016 |
| AU | 2011335882 | B2 | 3/2016 |
| CA | 2507406 | A1 | 5/2004 |
| CA | 2702650 | A1 | 9/2008 |
| CN | 1860104 | A | 11/2006 |
| CN | 101600697 | A | 12/2009 |
| CN | 101861313 | A | 10/2010 |
| CN | 104030990 | A | 9/2014 |
| EP | 2152701 | B1 | 11/2015 |
| IN | 282013 | B | 9/2015 |
| JP | 2003502406 | A | 1/2003 |
| JP | 2006508107 | A | 3/2006 |
| JP | 2006512314 | A | 4/2006 |
| JP | 2007500179 | A | 1/2007 |
| JP | 2009525337 | A | 7/2009 |
| JP | 2010520892 | A | 6/2010 |
| JP | 5746388 | B2 | 7/2015 |
| JP | 5940700 | B2 | 6/2016 |
| KR | 20090128478 | A | 12/2009 |
| KR | 101737753 | B1 | 5/2017 |
| MX | 2009009792 | A | 9/2009 |
| RU | 2295329 | C2 | 3/2007 |
| RU | 2498983 | | 11/2013 |
| RU | 2498983 | C2 | 11/2013 |
| WO | 1997019065 | A1 | 5/1997 |
| WO | 2000078731 | A1 | 12/2000 |
| WO | 2001029009 | A1 | 4/2001 |
| WO | 2002046171 | A2 | 6/2002 |
| WO | 2002060492 | A1 | 8/2002 |
| WO | 2002079197 | A1 | 10/2002 |
| WO | 2003022244 | A1 | 3/2003 |
| WO | 2003099796 | A1 | 12/2003 |
| WO | 2004016597 | A2 | 2/2004 |
| WO | 2004041789 | A1 | 5/2004 |
| WO | 2004041810 | A1 | 5/2004 |
| WO | 2004041814 | A1 | 5/2004 |
| WO | 2005012262 | A1 | 2/2005 |
| WO | 2006044457 | A1 | 4/2006 |
| WO | 2007089768 | A2 | 8/2007 |
| WO | 2007101232 | A2 | 9/2007 |
| WO | 2008099074 | A1 | 8/2008 |
| WO | 2008109943 | A1 | 9/2008 |
| WO | 2009029998 | A1 | 3/2009 |
| WO | 2009032861 | A1 | 3/2009 |
| WO | 2009073575 | A2 | 6/2009 |
| WO | 2010017122 | A2 | 2/2010 |
| WO | 2010063292 | A1 | 6/2010 |
| WO | 2012071612 | A1 | 6/2012 |
| WO | 2012149602 | A1 | 11/2012 |
| WO | 2014000032 | A1 | 1/2014 |
| WO | 2014051056 | A1 | 4/2014 |
| WO | 2014110189 | A1 | 7/2014 |
| WO | 2014114274 | A1 | 7/2014 |
| WO | 2015191846 | A1 | 12/2015 |

OTHER PUBLICATIONS

Alas, S. et al. (Jan. 2003). "Inhibition of Constitutive STAT3 Activity Sensitizes Resistant Non-Hodgkin's Lymphoma and Multiple Myeloma to Chemotherapeutic Drug-Mediated Apoptosis," Clinical Cancer Research, 9:316-326.

Alekseev, V.V., "Optical Isomeria and Pharmacological Activity of Medicines," Military Medical Academy, 1998, 6 pages [Online] [Retrieved Oct. 31, 2019], Retrieved from the internet.

Anastassiadis, T. et al. (Nov. 2011, e-pub. Oct. 30, 2011). "Comprehensive Assay of Kinase Catalytic Activity Reveals Features of Kinase Inhibitor Selectivity," Nature Biotechnology, 29(11):1039-1045.

Australian Notice of Acceptance dated Nov. 26, 2012 for Australian Patent Application No. 12008226327, 3 pages.

Australian Office Action dated Aug. 11, 2014 for Australian Patent Application No. 2012250491, 7 pages.

Australian Office Action dated Jun. 16, 2014 for Australian Patent Application No. 2011335882, 4 pages.

Australian Office Action dated Oct. 24, 2011 for Australian Patent Application No. 2008226327, 4 pages.

Berger, L.C. et al. (Jul. 15, 1994). "Tyrosine Phosphorylation of JAK-TYK Kinases in Malignant Plasma Cell Lines Growth-Stimulated by Interleukins 6 and 11," Biochemical and Biophysical Research Communications, 1202 (1):596-605.

Burger, R. et al. (Jan. 2009). "Janus Kinase Inhibitor INCB20 has Antiproliferative and Apoptotic Effects on Human Myeloma Cells In Vitro and In Vivo," Mol Cancer Ther, 8(1):26-35.

Burns, C.J. et al. (2009, e-pub. Aug. 23, 2009). "Phenylaminopyrimidines as Inhibitors of Janus Kinases (JAKs)," Bioorganic & Medicinal Chemistry Letters, 19:5887-5892.

Caira, M.R., "Crystalline Polymorphism of Organic Compounds," 1998, Topics in Current Chemistry, vol. 198, pp. 163-208.

Canadian Office Action dated Feb. 24, 2014 for Canadian Application No. 2,702,650, 4 pages.

Certificate of Patent mailed on Oct. 9, 2013 for Indonesian Patent Application No. W-00200902848, 2 pages.

Chabner, B.A. et al. (2006). "Chemotherapy of Neoplastic Diseases. Antineoplastic Agents," Section IX, Chapter 51 in Goodman &

(56) References Cited

OTHER PUBLICATIONS

Gilman's: The Pharmacological Basis of Therapeutics, 11 TH Edition, Brunton, L.L. et al. eds., McGraw-Hill Medical Publishing Division, pp. 1315-1403.
Chatterjee, M. et al. (Dec. 2004). "Combined Disruption of Both the MEK/ERK and the IL-6R/STAT3 Pathways is Required to Induce Apoptosis of Multiple Myeloma Cells in the Presence of Bone Marrow Stromal tells," Blood, 104(12):3712-3721.
Chatterjee, M. et al. (Nov. 1, 2002). "In the Presence of Bone Marrow Stromal Cells Human Multiple Myeloma Cells Become Independent of the IL-6/gp130/STAT3 Pathway," Blood, 100(9):3311-3318.
Cheung, W.C. et al. (2001). "The Bone Marrow Stromal Microenvironment Influences Myeloma Therapeutic Response In Vitro," Leukemia, 15:264-271.
Chinese Certificate of Invention Patent for Chinese Patent Application No. 200880015782.9, dated Jun. 4, 2014, 2 pages.
Chinese Fifth Office Action dated Nov. 21, 2013 for Chinese Patent Application No. 1200880015782.9, 4 pages.
Chinese First Office Action dated Sep. 22, 2011 for Chinese Patent Application No. 1200880015782.9, 24 pages.
Chinese Fourth Office Action dated Sep. 3, 2013 for Chinese Patent Application No. 1200880015782.9, 6 pages.
Chinese Notice of Granting Patent Right for Invention for Chinese Patent Application No. 200880015782.9, dated Mar. 5, 2014, 2 pages.
Chinese Second Office Action dated Jun. 12, 2012 for Chinese Patent Application No. 1200880015782.9, 7 pages.
Chinese Third Office Action dated Dec. 17, 2012 for Chinese Patent Application No. 1200880015782.9, 8 pages.
Daley, G.Q. et al. (Dec. 1988). "Transformation of an Interleukin 3-Dependent Hematopoietic Cell Line by the Chronic Myelogenous Leukemia-Specific P21 Obcriabl Protein," Proc. NaU. Acad Sci. USA, 85:9312-9316.
Dalton, W et al. (Nov. 15, 2006). "Synopsis of a Roundtable on Validating Novel Therapeutics for Multiple Myeloma," Clinical Cancer Research, 12(22):6603-6610.
De Vos, J. et al. (2000). "JAK2 Tyrosine Kinase Inhibitor Tyrphostin AG490 Downregulates the Mitogen-Activated Protein Kinase (MAPK) and Signal Transducer and Activator of Transcription (STAT) Pathways and Induces Apoptosis in Myeloma Cells" British Journal Haematology. 109:823-828.
Emanuel, S. et al. (2004). "A Vascular Endothelial Growth Factor Receptor-2 Kinase Inhibitor Potentiates the Activity of the Conventional Chemotherapeutic Agents Paclitaxel and Doxorubicin in Tumor Xenograft Models," Molecular Pharmacology 66(3):635-64 7.
European Communication from the Examining Division for European Patent Application No. 08714386.3, dated May 16, 2014, 4 pages.
European Communication pursuant to rules 161 (2) and 162 EPC dated Dec. 20, 2013 for European App. No 12779619.1, 3 pages.
European Extended Search Report for European App. No. 11845391.9, dated May 19, 2014, 7 pages.
European Extended Search Report for European Patent Application No. 08714386.3, dated May 25, 2011, 10 pages.
Examination Report dated Jun. 24, 2015 for New Zealand Appl. No. 611654.
Examination Report dated Jun. 24, 2015 for New Zealand Divisional Appl. No. 708964.
Examination Report dated Aug. 25, 2015 for Australian Appl. No. 2011335882.
Ferlin, M. et al. (Nov. 2000). "Insulin-Like Growth Factor Induces the Survival and Proliferation of Myeloma Cells Through an Interleukin-6-Independent Transduction Pathway," British Journal of Haematology, 111 (2):626-634.
Ferrajoli, A. et al. (Dec. 1, 2007). "WP1066 Disrupts Janus Kinase-2 and Induces Caspase-Dependent Apoptosis in Acute Myelogenous Leukemia Cells," Cancer Res, 67(23):11291-11299.
First Examination Report dated Sep. 22, 2014 for Indian Patent Application No. 3543/KOLNP/2009, 2 pages.
First Office Action with Search Report dated Sep. 4, 2014 for CN Application No. 201280021432X, with English translation (15 pages).
French, J.D. et al. (2003). "Transactivation of gp130 in Myeloma Cells," The Journal of Immunology, 170:7, DD. 3717-3723.
Gen Bank Accession No. NP_004963, last updated on Feb. 2, 2014, located at httD://www.ncbi.nlm.nih.aov/Drotein/NP 004963, last visited on Jun. 18, 2019, 5 pages.
Gomez-Benito, M. et al. (2007, e-pub. Dec. 8, 2006). "Mechanism of Apoptosis Induced by IFN-a in Human Myeloma Cells: Role of Jak1 and Bim and Potentiation by Rapamycin," Cellular Signaling, 19:844-854.
Gu, C.H. et al., "Grouping solvents by statistical analysis of solvent property parameters: implication to polymorph screening", International Journal of Pharmaceutics, 2004, vol. 283, No. 1-2, pp. 117-125.
Guillory, K., "Generation of polymorphs, hydrates, solvates and amorphous solids," Drugs and Pharmaceutical Sciences, 1999, vol. 95, pp. 183-226.
Gust, R. et al. (Jan.-Feb. 2001). "Vascular Remodeling in Experimentally Induced Subacute Canine Pulmonary Hypertension," Experimental Lung Research, 27:1-12.
Hartwig, J.F. (1998). "Transition Metal Catalyzed Synthesis of Arylamines and Aryl Ethers from Aryl Halides and Triflates: Scope and Mechanism," Angew. Chem. Int. Ed., 37:2046-2067.
Hat A, H. et al. (Jun. 15, 1993). "Interleukin-6 Gene Expression in Multiple Myeloma: A Characteristic of Immature Tumor Cells," Blood, 81(12):3357-3364.
Indian Patent Office, Office Action, Indian Application No. 201627044989, dated Nov. 28, 2019, 7 pages.
Indonesian Office Action dated Apr. 30, 2013 for Indonesian Patent Application No. W-00200902848, 2 pages.
International Preliminary Report on Patentability Chapter I Authority dated Sep. 15, 2009, for PCT Patent Application No. PCT/AU2008/000339, filed Mar. 12, 2008, 10 pages.
Pardanani, A. et al., "Update On The Long-Term Efficacy and Safety Of Momelotinib, a JAK1 and JAK2 Inhibitor, For The Treatment Of Myelofibrosis," Blood Journal, 2013, vol. 122, pp. 1-4.
Pedranzini, L. et al. (Oct. 1, 2006). "Pyridone 6, A Pan-Janus-Activated Kinase Inhibitor, Induces Growth Inhibition of Multiple Myeloma Cells," Cancer Res, 66(19):9714-9721.
Perez, L.E. et al. (2008). "Bone Marrow Stroma Confers Resistance to Apo2 Ligand/TRAIL in Multiple Myeloma in Part by Regulating c-FLIP," The Journal of Immunology, 180:1545-1555.
Pesu, M. et al. (Jun. 2008). "Therapeutic Targeting of Janus Kinase," Immunol Rev., 223:132-142.
Poupaert, J.H. (2007). "Drug Design: Basic Principles and Applications," Encyclopedia of Pharmaceutical Technology, pp. 1362-1369.
Puthier, D. et al. (1999). "IL-6 Up-Regulates Mcl-1 in Human Myeloma Cells Through JAK/STAT Rather Than Ras/MAP Kinase Pathway," Eur. J. Immunol. 29:3945-3950.
Rane, S.G. et al. (2000). "Janus Kinases: Components of Multiple Signaling Pathways," Oncogene, 19:5662-679.
Russian Office Action dated Dec. 11, 2012 for Russian Patent Application No. 2009137363/04(052832), 12 pages.
Scott, L.M. et al. (Feb. 1, 2007). "JAK2 Exon 12 Mutations in Polycythemia Vera and Idiopathic Erythrocytosis," The New England Journal of Medicine, 356(5):459-468.
Scuto, A. et al. (2011, e-pub. Dec. 17, 2010). "The Novel JAK Inhibitor AZD1480 Blocks STAT3 and FGFR3 Signaling, Resulting in Suppression of Human Myeloma Cell Growth and Survival," Leukemia, 25:538-50.
Search Reports—Intl. Preliminary Report on Patentability—Written Opinion dated Jun. 4, 2013 for PCT/AU2011/001551.
Serajuddin, Salt formation to improve drug solubility, Advanced Drug Delivery Reviews, 2007, 59, pp. 603-616.
Shin-Seizaigaku, "New Pharmaceutical Science," Modern Pharmaceutics, 1984, pp. 102-103, 232-233.

(56) References Cited

OTHER PUBLICATIONS

Stahly, P., "The Importance of Salt Selection and Polymorph Screening for the Drug Product." Journal of Pharmaceutical Science and Technology, Japan, 2006, vol. 66, No. 6, pp. 435-439.
Stille, J.K. (1986). "The Palladium-Catalyzed Cross-Coupling Reactions of Organotin Reagents with Organic Electrophiles," Angew. Chem. Int. Ed. Engl., 25:508-524.
Stoimenovski, "Crystalline vs. Ionic Liquid Forms of Active Pharmaceutical Ingredients: A Position Paper," Pharmaceutical Research, 27(4):521-526, Apr. 2010.
Supplementary European Search Report for EP Application No. EP 08714386.3, dated May 6, 2011, 10 pages.
Taylor, H.E. et al. (Jan. 1998, e-pub. Jan. 2, 1998). "1-Aikylcarbonyloxymethyl Prod rugs of 5-Fluorouracil (5-FU): Synthesis, Physicochemical Properties, and Topical Delivery of 5-FU," Journal of Pharmaceutical Sciences, 87 (1):15-20.
Thabard, W et al. (Jun. 21, 2001). "IL-6 Upregulates Its Own Receptor on Some Human Myeloma Cell Lines," Cytokine, 14(6):352-356.
Translation of Office Action dated Dec. 15, 2014 for Japanese Patent Application No. 2014/018467 (13 pages).
Traynor, A.M. et al. (2004). "Systemic Treatment of Advanced Non-Small Cell Lung Cancer," Drugs of Today, 40 (8):697-710.
Tyner, J.W et al. (Jun. 24, 2010). "CYT387, A Novel JAK2 Inhibitor, Induces Hematologic Responses and Normalizes Inflammatory Cytokines in Murine Myeloproliferative Neoplasms," Blood, 115(25):5232-5240.
Tyukavkina, N.A. et al. (2005). Bioorganicheskaya Khimiya, 41 Edition, Moscow, Drofa, pp. 83-85, with English Translation.
Vannucchi, A.M. et al. (May/Jun. 2009). "Advances in Understanding and Management of Myeloproliferative Neoplasms," CA Cancer J Clin, 59(3):171-191.
Wermuth, C.G. et al., "Selected procedures for the preparation of pharmaceutically acceptable salts," Handbook of Pharmaceutical Salts: Properties, Selection and Use, 2002, pp. 249-263.
Wheelhouse, R.T. et al. (2006). "Design, Synthesis, and Evaluation of Novel Biarylpyrimidines: A New Class of Ligand for Unusual Nucleic Acid Structures," J. Med. Chem., 9(17):5187-5198.
Written Opinion dated Feb. 21, 2012 for PCT Patent Application No. PCT/AU2011 /001551, filed Nov. 29, 2011, 8 pages.
Written Opinion of International Searching Authority dated May 22, 2012 for PCT Patent Application No. PCT/AU2012/000462, filed May 1, 2012, 3 pages.
Written Opinion of International Searching Authority dated Sep. 6, 2013 for PCT Patent Application No. PCT/AU2013/000687, filed Jun. 26, 2013, 5 pages.
Written Opinion of the International Search Authority dated May 15, 2008 for PCT Application No. PCT/AU2008/000339, filed Mar. 12, 2008, 9 pages.
Written Opinion of the ISR dated Feb. 21, 2012 for International Application No. PCT/AU2011/001552, International Filing Date: Nov. 29, 2011, Applicant: YM Biosciences Australia PTY Ltd, et al., 8 pages.
Zhang, X.G. et al. (Jun. 15, 1994). "Reproducible Obtaining of Human Myeloma Cell Lines as a Model for Tumor Stem Cell Study in Human Multiple Myeloma," Blood, 83(12):3654-3663.
Zhu, Z. et al., "Inhibition of KRAS-driven tumorigenicity by interruption of an autocrine cytokine circuit," Cancer Discovery, Apr. 2014, vol. 4, No. 4, pp. 452-465.
International Preliminary Report on Patentability dated Jun. 4, 2013 for PCT Patent Application No. PCT/AU2011/001551, filed Nov. 29, 2011, 9 pages.
International Preliminary Report on Patentability dated Nov. 5, 2013 for PCT Patent Application No. PCT/AU2012/000462, filed May 1, 2012, 4 pages.
International Search Report dated Feb. 21, 2012 for International Patent Application No. PCT/AU2011/001551, International Filing Date: Nov. 29, 2011, 8 pages.
International Search Report dated Feb. 21, 2012 for PCT Patent Application No. PCT/AU2011/001551, filed Nov. 29, 2011, 7 pages.
International Search Report dated May 15, 2008 for PCT Patent Application No. PCT/AU2008/000339, filed Mar. 12, 2008, 4 pages.
International Search Report dated May 22, 2012 for PCT Patent Application No. PCT/AU2012/000462, filed Jun. 26, 2013, 2 pages.
International Search Report dated Sep. 6, 2013 for PCT Patent Application No. PCT/AU2013/000687, filed Jun. 26, 2013, 4 pages.
Invitation to Correct Defects in the International Application dated Jan. 3, 2014, for PCT Patent Application No. PCT/AU2013/000687, filed Jun. 26, 2013, 6 pages.
Israel Patent Office, Office Action, Israeli Patent Application No. 249038, dated Dec. 12, 2018, nine pages.
Japanese Notice of Final Rejection dated Mar. 3, 2014 for Japanese Patent Application No. 2009-552972, With English translation, 4 pages.
Japanese Office Action dated Apr. 26, 2019 for Japanese Patent Application No. 2016-572271, English translation, 6 pages.
Japanese Office Action dated Mar. 19, 2013 for Japanese Patent Application No. 2009-552972, with English translation, 8 pages.
Japanese Office Action dated Oct. 15, 2013 for Japanese Patent Application No. 2009-552972, 3 pages.
Japanese Office Action dated Sep. 1, 2014 for Japanese Patent Application No. 2013-541149, with English translation, 5 pages.
Jelinek, D.F. et al. (Nov. 1, 1993). "Coexistence of Aneuploid Subclones Within a Myeloma Cell Line That Exhibits Clonal Immunoglobulin Gene Rearrangement: Clinical Implications," Cancer Research, 53:5320-327.
Khong, T. et al. (2008). "The Effect of Azacitidine on Interleukin-6 Signaling and Nuclear Factor-kB Activation and Its In Vitro and In Vivo Activity Against Multiple Myeloma," Haematologica, 93(6):860-869.
Klein, B. et al. (Feb. 1989). "Paracrine Rather Than Autocrine Regulation of Myeloma—Cell Growth and Differentiation by Interleukin-6," Blood, 73(2):517-526.
Korean Office Action dated Jul. 3, 2014 for Korean Patent Application No. 10-2009-7021274, 4 pages.
Kralovics, R. et al. (Apr. 28, 2005). "A Gain-of-Function Mutation of JAK2 in Myeloproliferative Disorders," The New England Journal of Medicine, 352(17):1779-1790.
Kumada, M. et al. (1988). "Phosphine-Nickel Complex Catalyzed Cross-Coupling of Grignard Reagents with Aryl and Alkenyl Halides: 1,2-Dibutylbenzene," Organic Syntheses, Collective vol. 6, pp. 407-411.
Kumar, (2009). "Kinase drug discovery approaches in chronic myeloproliferative disorders" Oncogene, 8:2305-2313.
Kumar, S. et al. (2005, e-pub. Jun. 16, 2005). "CD45 Expression by Bone Marrow Plasma tells in Multiple Myeloma: Clinical and Biological Correlations," Leukemia, 19:1466-1470.
Levine, R.L. et al. (Apr. 2005). "Activating Mutation in the Tyrosine Kinase JAK2 in Polycythemia Vera, Essential Thrombocythemia, and Myeloid Metaplasia with Myelofibrosis," Cancer Cell, 7:387-397.
Li, J. et al. (Jan. 2010). "INCB16562, a JAK½ Selective Inhibitor, Is Efficacious Against Multiple Myeloma tells and Reverses the Protective Effects of Cytokine and Strom al Cell Support," Neoplasia, 12(1) :28-38.
Lucet, I.S. et al. (Jan. 1, 2006, e-pub. Sep. 20, 2005). "The Structural Basis of Janus Kinase 2 Inhibition by a Potent and Specific Pan-Janus Kinase Inhibitor," Blood, 107(1):176-183.
March, J. (1992). "Aliphatic Nucleophilic Substitution," in Advanced Organic Chemistry: Reactions, Mechanisms, and Structure, 4th Edition, John Wiley & Sons, New York, pp. 352-357.
Mashkovskiy, M.D. (1993). "Lekarstvennyye Sredstva," Moscow Meditsina Part 1, p. 8, with English Translation.
Mexican Patent Office, Office Action, Mexican Application No. MX/a/2016/016294, dated Oct. 24, 2019, 11 pages.
Miyaura, N. et al. (1995). "Palladium-Catalyzed Cross-Coupling Reactions of Organoboron Compounds," Chem. Rev., 95(7):2457-2483.

(56) References Cited

OTHER PUBLICATIONS

Monaghan, K. et al. (2011, e-pub. Nov. 12, 2009). "CYT997 Causes Apoptosis in Human Multiple Myeloma," Invest New Drugs, 29:232-238.
Moreau, P. et al. (May 2004). "Patients with CD45 Negative Multiple Myeloma Receiving High-Dose Therapy Have a Shorter Survival than those with CD45 Positive Multiple Myeloma," Haematologica, 89(5):547-551.
Moreaux, J. et al. (Apr. 15, 2004). "BAFF and APRIL Protect Myeloma Cells from Apoptosis Induced by Interleukin 6 Deprivation and Dexamethasone," Blood, 103(8):3148-3157.
Mullighan, C.G. et al. (Jun. 9, 2009). "JAK Mutations in High-Risk Childhood Acute Lymphoblastic Leukemia," PNAS, 106(23):9414-9418.
Muwakkit, S. et al. (2010) L-Asparaginase-Induced Pancreatitis in Children with Acute Lymphoblastic Leukemia: Is Allopurinol Protective? Pediatric Hematology and Oncology 27(6); 496-501.
Negishi, E. (Jul. 1, 2002). "A Genealogy of Pd-Catalyzed Cross-Coupling," Journal of Organometallic Chemistry, 653:34-40.
Office Action dated Feb. 13, 2015 for Eurasian Appl. No. 201390815.
Office Action dated Mar. 11, 2015 for Canadian Patent Application No. 2,702,650 (3 pages).
Office Action dated Apr. 13, 2015 for Japanese Appl. No. 2013-514449.
Office Action dated Jun. 23, 2015 for Chinese Appl. No. 201180063989.5.
Office Action dated Jun. 23, 2015 for Chinese Patent Application No. 201410208369.1.
Office Action dated Jun. 26, 2015 for Mexican Appl. No. MX/a/2013/006261.
Office Action dated Jul. 1, 2015 for Korean Patent Application No. 10-2015-700927 4.
Office Action dated Aug. 25, 2015 for Eurasian Appl. No. 201390815.
Office Action dated Feb. 29, 2016 for Chinese Patent Application No. 20140578333.2.
Office Action dated Mar. 29, 2016 for Eurasian Patent Application No. 201390815.
Office Action dated Oct. 22, 2015 from U.S. Appl. No. 14/736,690.
Pardanani, A. et al. (2009, e-pub. Mar. 19, 2009). "CYT387, a Selective JAK1/JAK2 Inhibitor: In Vitro Assessment of Kinase Selectivity and Preclinical Studies Using Cell Lines and Primary Cells From Polycythemia Vera Patients," Leukemia, 23:1441-1445.
Pardanani, A. et al. (2010). "A Phase 1/11 Study of CYT387, An Oral JAK-½ Inhibitor, In Myelofibrosis: Significant Response Rates In Anemia, Splenomegaly, and Constitutional Symptoms," Blood (ASH AnnualMeeting Abstracts). 116:Abstract 460.
Pardanani, A. et al., "JAK inhibitor therapy for myelofibrosis: critical assessment of value and limitations," Leukemia 25:218-225, Nov. 16, 2010.
Extended European Search Report issued in European Patent Application No. 21174463.6, dated Sep. 29, 2021 (10 pages).
Andriopoulos et al., "BMP6 is a key endogenous regulator of hepcidin expression and iron metabolism," Nat Genet, Mar. 1, 2009, 41(4): 482-7.
Berge, at al., "Pharmaceutical Salts," Journal of Pharmaceutical Science, Jan. 1977, 66(1), 19 pages.
CAS No. 191732-72-6, "Lenalidomide," Cayman Chemical, retrieved on Jul. 28, 2022, retrieved from URL<https://www.caymanchem.com/product/14643/lenalidomide>, 1 pages.
CAS No. 50-35-1, "Thalidomide," Santa Cruz Biotechnology, retrieved on Jul. 28, 2022, retrieved from URL<https://www.scbt.com/p/thalidomide-50-35-1>, 6 page.
Cheson et al., "Monoclonal Antibody Therapy for B-Cell Non-Hodgkin's Lymphoma," The New England Journal of Medicine, Aug. 7, 2008, 359(6), p. 613-626.
Ferrara et al., "Clinical application of angiogenic growth factors and their inhibitors." Nature America Inc., Dec. 1999, Medicine, 5:1359-1364.
Foster, "Deuterium Isotope Effects in Studies of Drag Metabolism", Trends Pharmacol. Sci., 1984, 5(12):524-527.
International Preliminary Report on Patentability in International Appln. No. PCT/US2015/035316, dated Dec. 15, 2016, 10 pages.
Morton et al., "Lymphoma Incidence Patterns by WHO Subtype in the United States, 1992-2001" Blood 2006, 107(1), p. 265-276.
Notice of Allowance in U.S. Appl. No. 14/736,690, dated May 16, 2006, 9 pages.
Wierda et al., "Current and Investigational Therapies for Patients with CLL," Hematology, Jan. 1, 2006, 285-294.
Wrana, "Signaling by the TGFβSuperfamily," Cold Spring Harb. Perspect. Biol, 2013, 5:a011197.
Zhao et al., "Iron regulation bv hepcidin," J Clin. Invest, 2013, 123(6):2337-43.
prnewswire.com [online], "YM Biosciences Reports Significant Response Rates in Anemia, Splenomegaly, and Constitutional Symptoms from the Phase 1/11 Trial of Its JAK1/JAK2 Inhibitor, CYT387, in Myelofibrosis," Nov. 8, 2010, retrieved on Sep. 29, 2022, retrieved from URL<https://www.prnewswire.com/news-releases/ym-biosciences-reports-significant-response-rates-in-anemia-splenomegaly-and-constitutional-symptoms-from-the-phase-iii-trial-of-its-jak1jak2-inhibitor-cyt387-in-myelofibrosis-106893443.html>, 5 pages.
International Search Report—Written Opinion dated Sep. 10, 2015 for PCT/US2015/035316.

* cited by examiner

N-(CYANOMETHYL)-4-(2-(4-MORPHOLINOPHENYLAMINO) PYRIMIDIN-4-YL)BENZAMIDE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 9,469,613.* This [application] *is an application for reissue of U.S. Pat. No. 9,469,613, issued on Oct. 18, 2016, and is a continuation of U.S. application Ser. No. 16/164,681, filed Oct. 18, 2018* (*now U.S. Pat. No. RE48,285*), *which is also an application for reissue of U.S. Pat. No. 9,469,613, which issued from U.S. application Ser. No. 14/736,690, filed on Jun. 11, 2015, which* claims the benefit and the priority of U.S. provisional patent application Ser. No. 62/011,315, filed Jun. 12, 2014, the disclosure*s* of *each of* which [is] *are* hereby incorporated herein by reference in [the] *their* entirety.

FIELD

The present application relates to stable novel salt forms of N-(cyanomethyl)-4-(2-(4-morpholinophenylamino)pyrimidin-4-yl)benzamide that are suitable for the preparation of pharmaceutical formulations thereof, and their therapeutic use.

BACKGROUND

The inhibition to Janus kinase (JAK) has been evaluated in treating hyperproliferative diseases. Several JAK inhibitors have been developed: ruxolitinib, tofacitinib, baricitinib, lestaurtinib, pacritinib, fedratinib, XL019, SB1518 and AZD1480 have been developed (Sonbol, Ther. Adv. Hematol. 4: 15-35, 2013). The compound N-(cyanomethyl)-4-(2-(4-morpholinophenylamino)pyrimidin-4-yl)benzamide (CYT-0387) is a JAK kinase inhibitor In clinical studies, CYT-0387 is effective in treating hyperproliferative diseases such as polycythemia vera (PV), essential thrombocythemia (ET), and primary myelofibrosis (PMF). Also, the patients having myelofibrosis who received CYT-0387 exhibited the improvement in the anemia and/or spleen responses (see U.S. Pat. No. 8,486,941 and Application Publication No. 2014-0073643, each of which is incorporated herein by reference in its entirety).

It is desired to have different forms of the compound that are suitable for the preparation of pharmaceutical formulations containing CYT-0387 and their therapeutic use.

BRIEF SUMMARY

The present invention is directed to novel CYT-0387 forms.

In one aspect, the present invention is directed to CYT-0387 monohydrochloride anhydrous Form I:

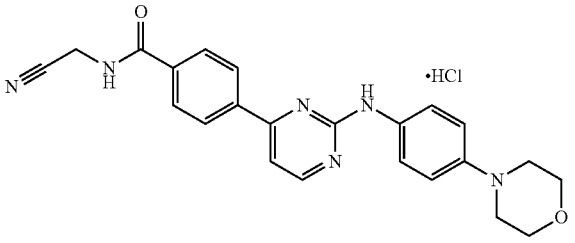

which has an X-ray powder diffraction (XRPD) pattern having peaks at about 13.5°, 20.9°, 26.1°, 26.6°, and 28.3° 2−θ±0.2°2−θ.

In another aspect, the present invention is directed to CYT-0387 dihydrochloride monohydrate Form II:

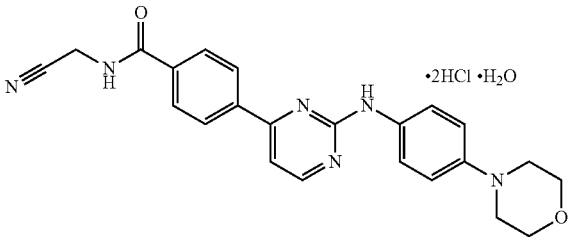

which has an X-ray powder diffraction (XRPD) pattern having peaks at about 7.7°, 19.3°, 24.0°, 25.7°, and 29.6° 2−θ±0.2°2−θ.

In another aspect, the present invention is directed to CYT-0387 monohydrochloride anhydrous Form III (Form III):

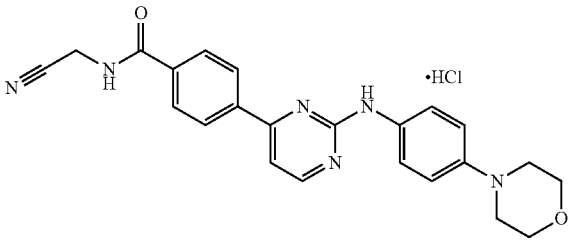

which has an X-ray powder diffraction (XRPD) pattern having peaks at about 12.7°, 14.6°, 17.8°, 19.7°, and 23.3° 2−θ±0.2°2−θ.

The invention also provides compositions, including pharmaceutical compositions, kits that include the compounds, and methods of using and making the pharmaceutical compositions. The pharmaceutical compositions provided herein are useful in treating diseases, disorders, or conditions that are mediated by JAK.

In one embodiment, the application is directed to dosage forms comprising CYT-0387 Form III, in particular dosage forms as a tablet, and more particularly dosage forms comprising comprises CYT-0387 Form III in an amount equivalent to from between 30-250 mg of CYT-0387 free base. In one embodiment, the dosage form comprises CYT-0387 Form II in an amount equivalent to 100-200 mg of CYT-0387 free base.

In further embodiments, the application is directed to dosage forms or pharmaceutical compositions comprising CYT-0387 Form III in an amount equivalent to 200 mg of CYT-0387 free base which provide a pharmacokinetic profile substantially similar to a dosage form or pharmaceutical composition comprising the CYT-0387 dihydrochloride anhydrous Form I in an amount equivalent to 300 mg of CYT-0387 free base.

In some embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to from between about 100 mg to about 300 mg of CYT-0387 free base. In certain embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to about 100 mg, about 150 mg, about 200 mg, about 250 mg, or about 300 mg of CYT-0387 free base. In certain embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to about 100 mg of CYT-0387 free base. In certain embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to about 200 mg of CYT-0387 free base. In certain embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to about 250 mg of CYT-0387 free base. In certain embodiments, the application is directed to dosage forms comprising CYT-0387 dihydrochloride monohydrate Form II, as a tablet, wherein the dosage forms comprising comprises CYT-0387 dihydrochloride monohydrate Form II in an amount equivalent to about 300 mg of CYT-0387 free base. In additional embodiments, the application is directed to dosage forms or pharmaceutical compositions comprising CYT-0387 dihydrochloride monohydrate Form II in an amount equivalent to 200 mg of CYT-0387 free base which provide a pharmacokinetic profile substantially similar to a dosage form or pharmaceutical composition comprising the CYT-0387 dihydrochloride monohydrate Form II in an amount equivalent to 300 mg of CYT-0387 free base.

Also provided is a kit that includes a compound of formula (I) or a pharmaceutically acceptable salt, isomer, or a mixture thereof. The kit may further comprise a label and/or instructions for use of the compound in treating a disease, disorder, or condition in a human in need thereof.

Also provided are articles of manufacture that include a compound of formula (I) or a pharmaceutically acceptable salt, isomer, or a mixture thereof, and a container. In one embodiment, the container may be a vial, jar, ampoule, preloaded syringe, or an intravenous bag.

DETAILED DESCRIPTION

The following description sets forth exemplary compositions and methods, parameters and the like. It should be recognized, however, that such description is not intended as a limitation on the scope of the present disclosure but is instead provided as a description of exemplary embodiments.

JAK inhibitors CYT-0387, N-(cyanomethyl)-4-(2-(4-morpholinophenylamino)pyrimidin-4-yl)benzamide, that is disclosed in U.S. Pat. No. 8,486,941 having the below structure:

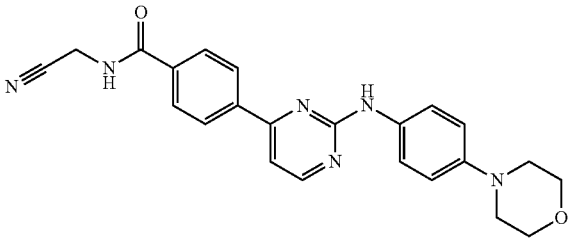

The dihydrochloride anhydrous form of CYT-0387 is disclosed in PCT Application WO 2012/071612. CYT-0387 dihydrochloride anhydrous has the below structure:

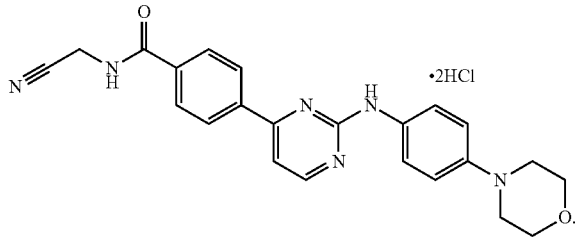

The XRPD, the differential scanning calorimetry (DSC), the thermogravimetric analysis (TGA), and the dynamic vapor sorption (DVS) of CYT-0387 dihydrochloride anhydrous form I (Form IV) are shown in FIGS. 1, 2, 3, and 4, respectively.

The present application provides other novel forms of CYT-387: monohydrochloride anhydrous Form I (Form I), dihydrochloride monohydrate Form II (Form II), and monohydrochloride anhydrous Form III (Form III).

As used herein, the terms "Form I" or "CYT-0387 Form I" are used to refer to CYT-0387 monohydrochloride anhydrous Form I; the terms "Form II" or "CYT-0387 Form II" are used to refer to CYT-0387 dihydrochloride hydrate, CYT-0387 dihydrochloride monohydrate, or CYT-0387 dihydrochloride monohydrate Form II; and the terms "Form III" or "CYT-0387 Form III" are used to refer to CYT-0387 monohydrochloride anhydrous Form III; and the terms "Form IV" or "CYT-0387 Form IV" are used to refer to CYT-0387 dihydrochloride anhydrous Form I.

Figure 6:
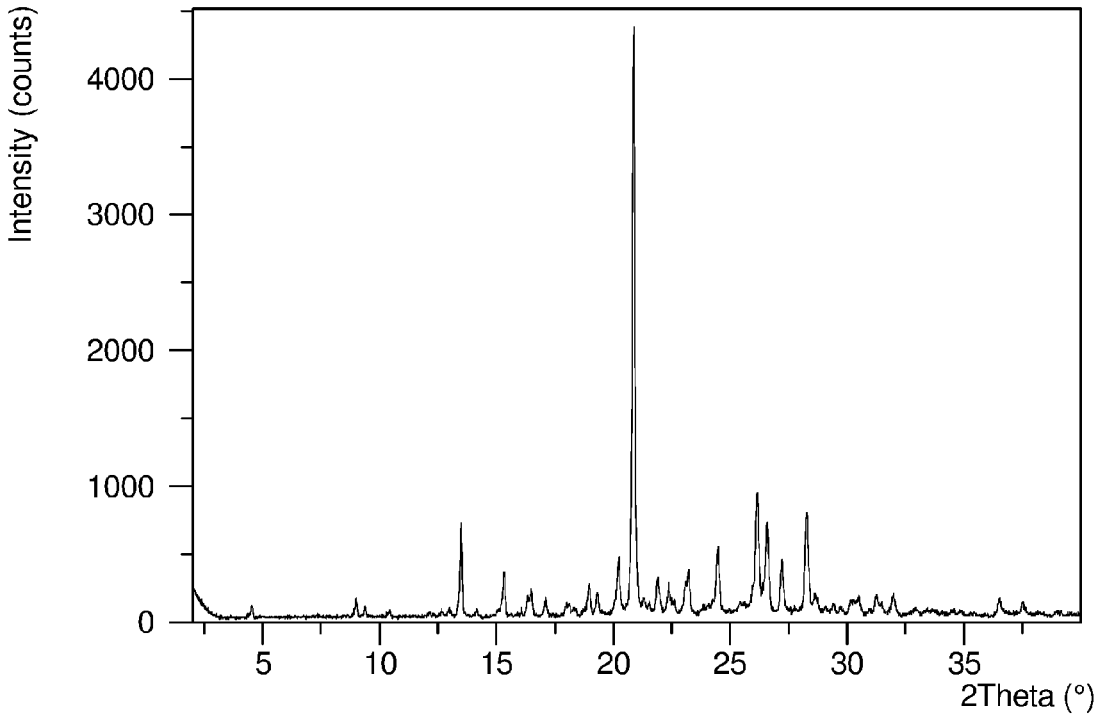
FIG. 6: XRPD pattern for N-(cyanomethyl)-4-(2-(4-morpholinophenylamino)pyrimidin-4-yl)benzamide monohydrochloride anhydrous Form I.
Figure 9:
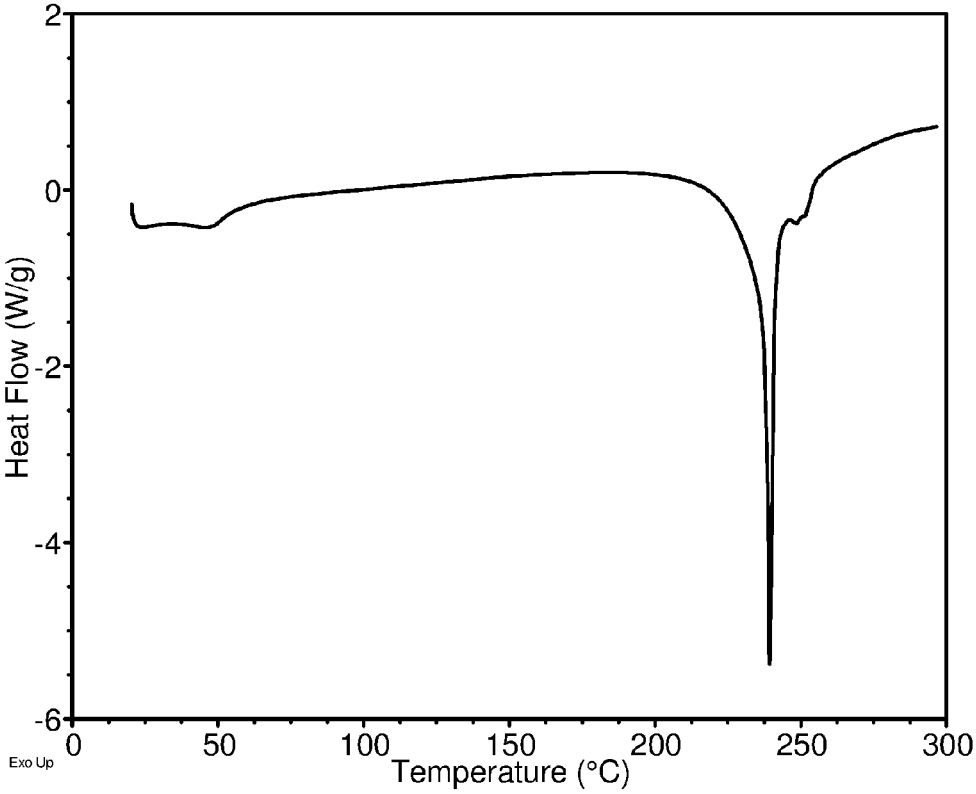
FIG. 9: DSC for N-(cyanomethyl)-4-(2-(4-morpholinophenylamino)pyrimidin-4-yl)benzamide monohydrochloride anhydrous Form I.
Figure 12:
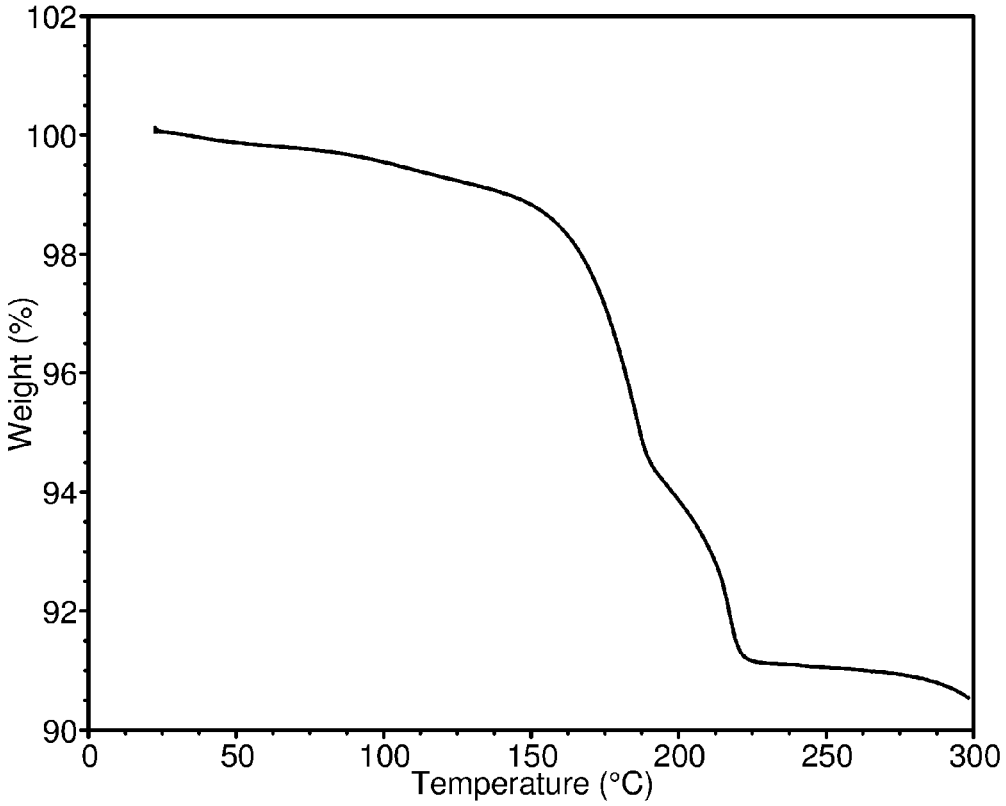
FIG. 12: TGA for N-(cyanomethyl)-4-(2-(4-morpholinophenylamino)pyrimidin-4-yl)benzamide monohydrochloride anhydrous Form I.

In one embodiment, Form I or CYT-0387 Form I is characterized by XRPD shown in FIG. 6, DSC in FIG. 9, or TGA in FIG. 12. In one embodiment, Form I or CYT-0387 Form I has an XRPD pattern having peaks at about 13.5°, 20.9°, 26.1°, 26.6°, and 28.3° 2−θ±0.2 °2−θ.

Figure 5:
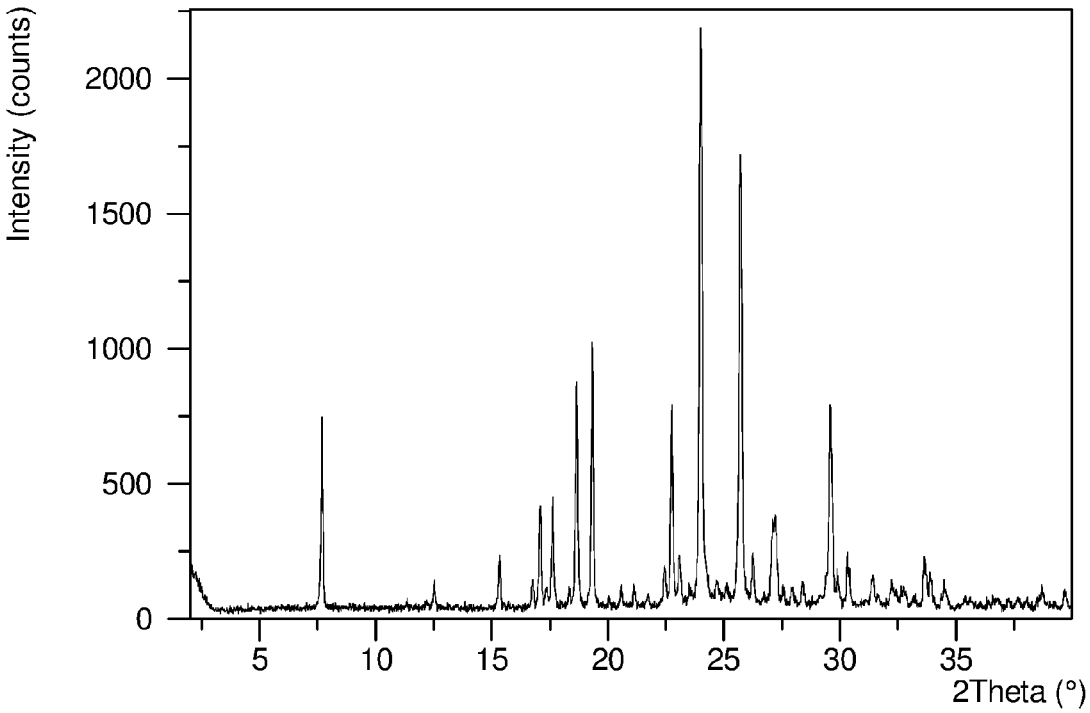
FIG. 5: XRPD pattern for N-(cyanomethyl)-4-(2-(4-morpholinophenylamino)pyrimidin-4-yl)benzamide dihydrochloride monohydrate Form II.
Figure 8:
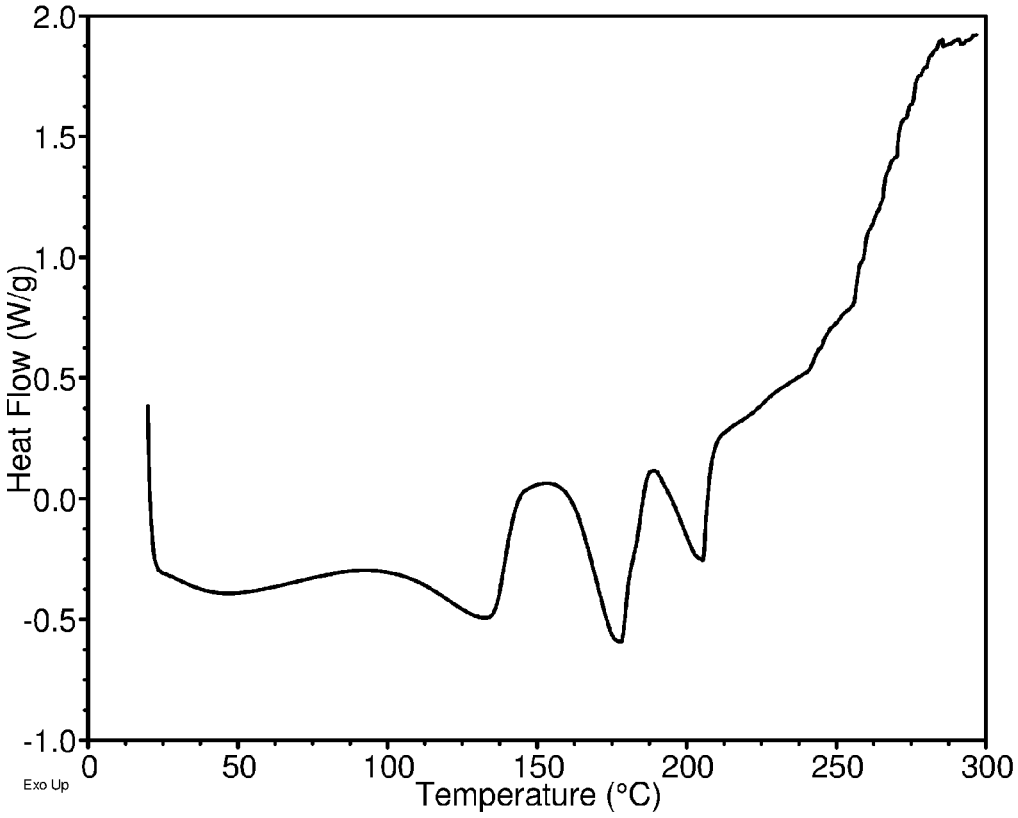
FIG. 8: DSC for N-(cyanomethyl)-4-(2-(4-morpholinophenylamino)pyrimidin-4-yl)benzamide dihydrochloride monohydrate Form II.
Figure 11:
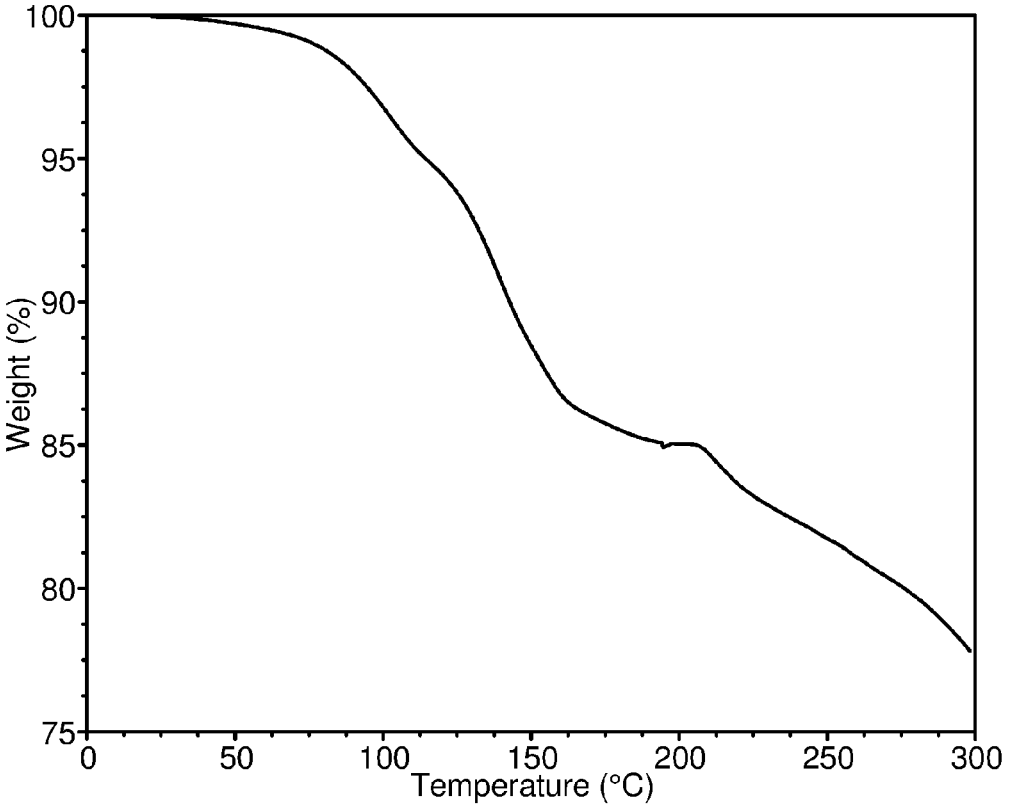
FIG. 11: TGA for N-(cyanomethyl)-4-(2-(4-morpholinophenylamino)pyrimidin-4-yl)benzamide dihydrochloride monohydrate Form II.
Figure 14:
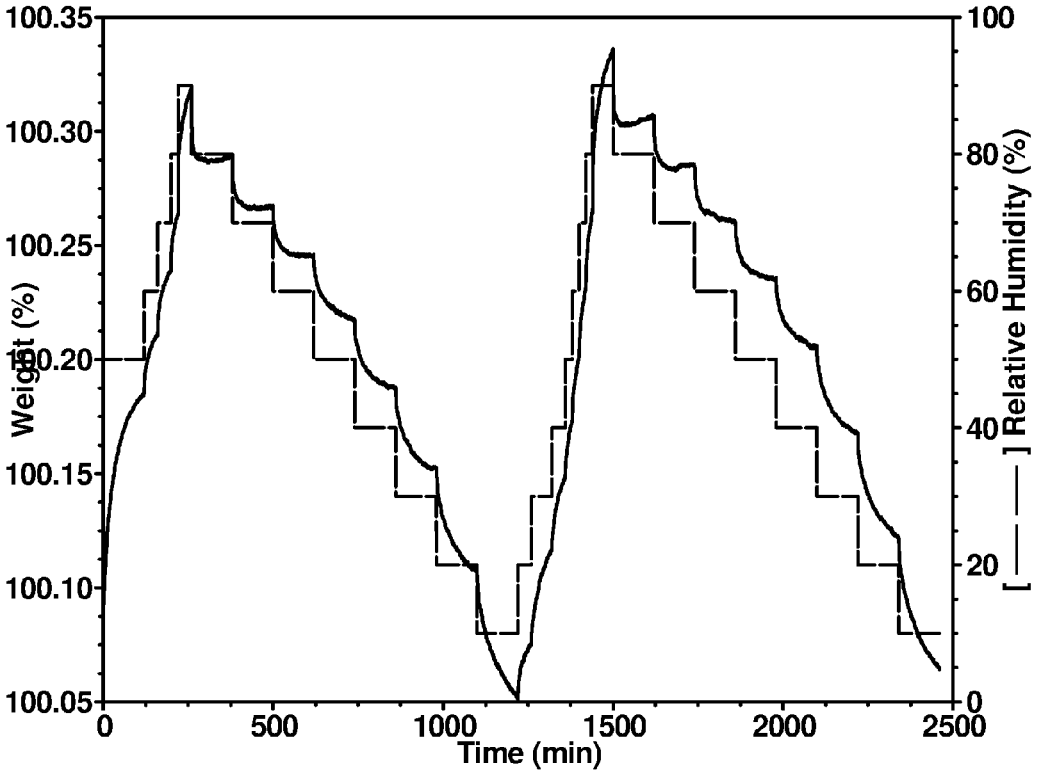
FIG. 14: DVS for N-(cyanomethyl)-4-(2-(4-morpholinophenylamino)pyrimidin-4-yl)benzamide dihydrochloride monohydrate Form II.

In some embodiment, Form II or CYT-0387 Form II is characterized by XRPD shown in FIG. 5, DSC in FIG. 8, TGA in FIG. 11, or DVS in FIG. 14. In one embodiment, Form II or CYT-0387 Form II has an XRPD pattern having peaks at about 7.7°, 19.3°, 24.0°, 25.7°, and 29.6° 2−θ±0.2°2−θ.

Figure 7:
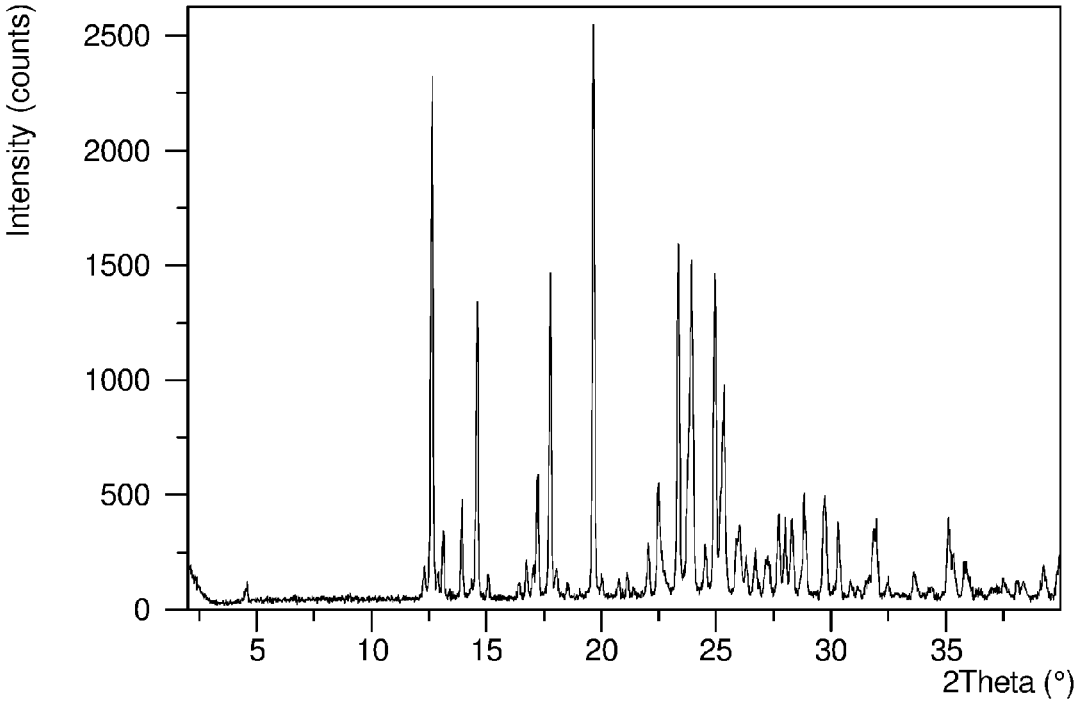
FIG. 7: XRPD pattern for N-(cyanomethyl)-4-(2-(4-morpholinophenylamino)pyrimidin-4-yl)benzamide monohydrochloride anhydrous Form III.
Figure 10:
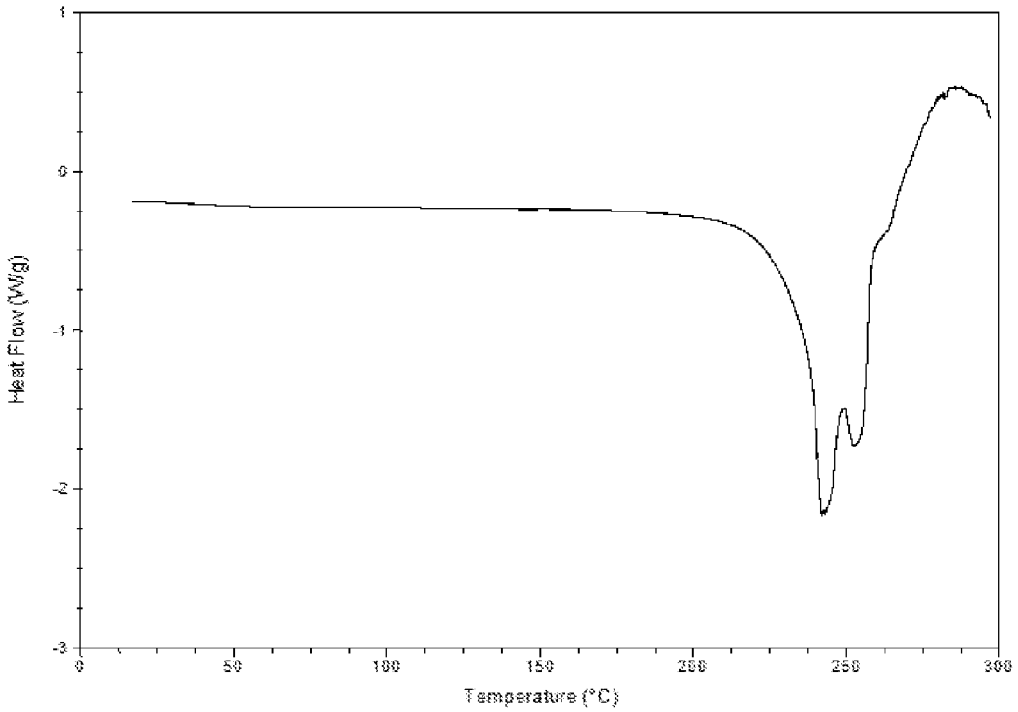
FIG. 10: DSC for N-(cyanomethyl)-4-(2-(4-morpholinophenylamino)pyrimidin-4-yl)benzamide monohydrochloride anhydrous Form III.
Figure 13:
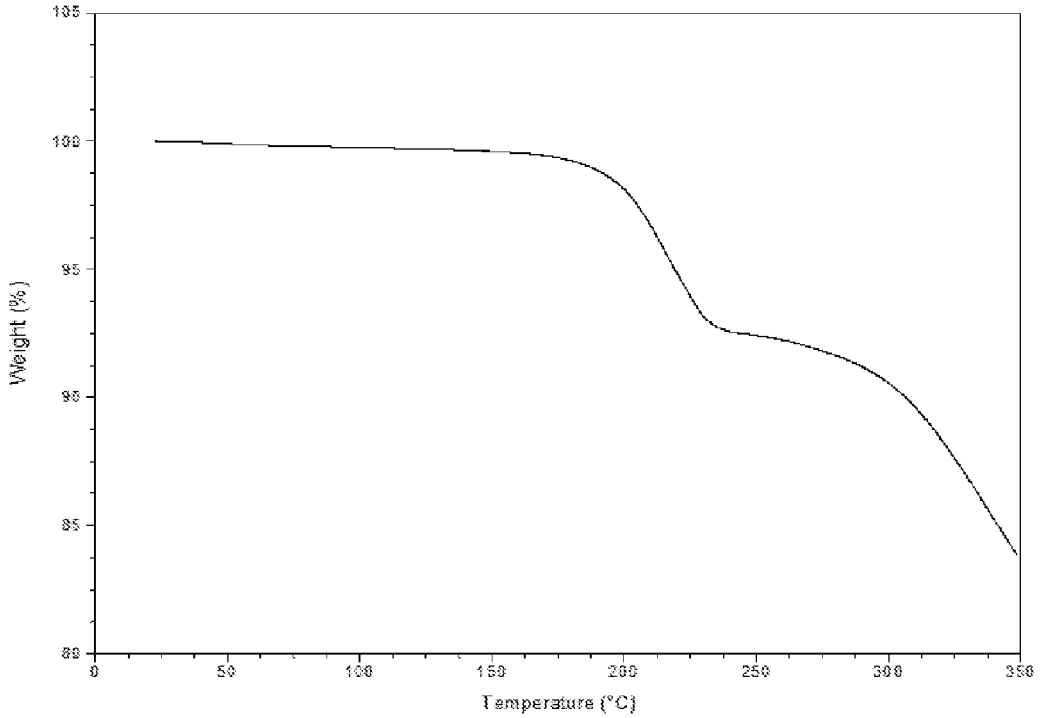
FIG. 13: TGA for N-(cyanomethyl)-4-(2-(4-morpholinophenylamino)pyrimidin-4-yl)benzamide monohydrochloride anhydrous Form III.

In other embodiment, Form III or CYT-0387 Form III is characterized by XRPD shown in FIG. 7, DSC in FIG. 10, or TGA in FIG. 13. In one embodiment, Form III or CYT-0387 Form III has an XRPD pattern having peaks at about 12.7°, 14.6°, 17.8°, 19.7°, and 23.3° 2−θ±0.2°2−θ.

Figure 1:
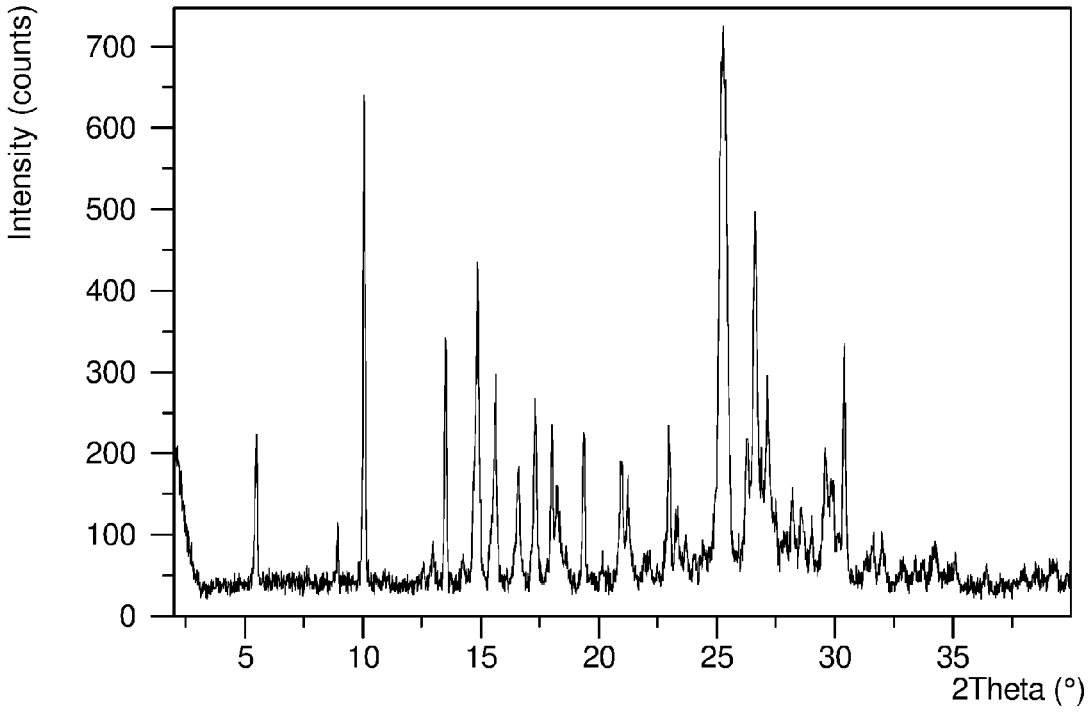
FIG. 1: XRPD of N-(cyanomethyl)-4-(2-(4-morpholinophenylamino)pyrimidin-4-yl)benzamide (CYT-0387) dihydrochloride anhydrous Form I.
Figure 2:
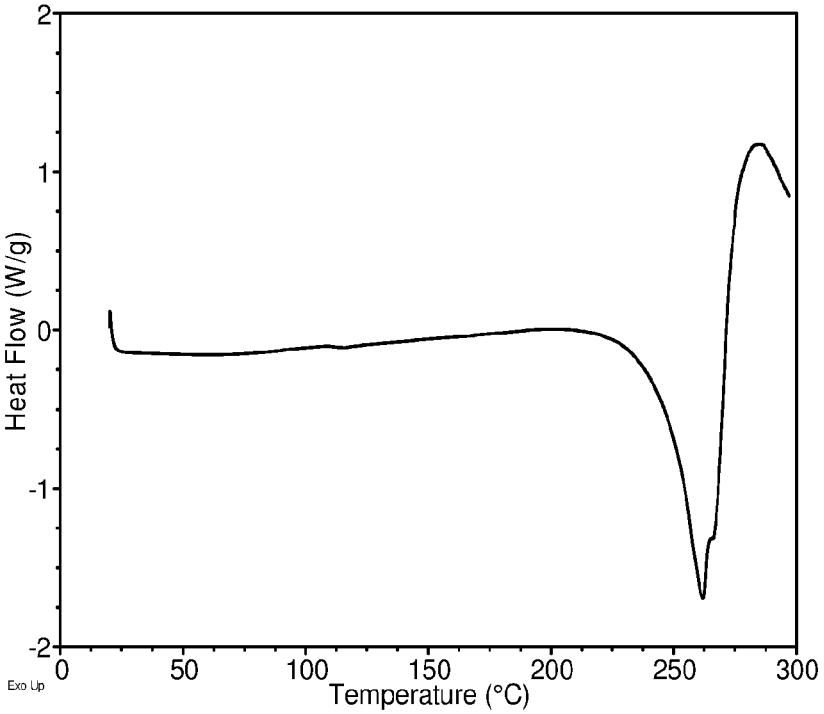
FIG. 2: DSC of N-(cyanomethyl)-4-(2-(4-morpholinophenylamino)pyrimidin-4-yl)benzamide (CYT-0387) dihydrochloride anhydrous Form I.
Figure 3:
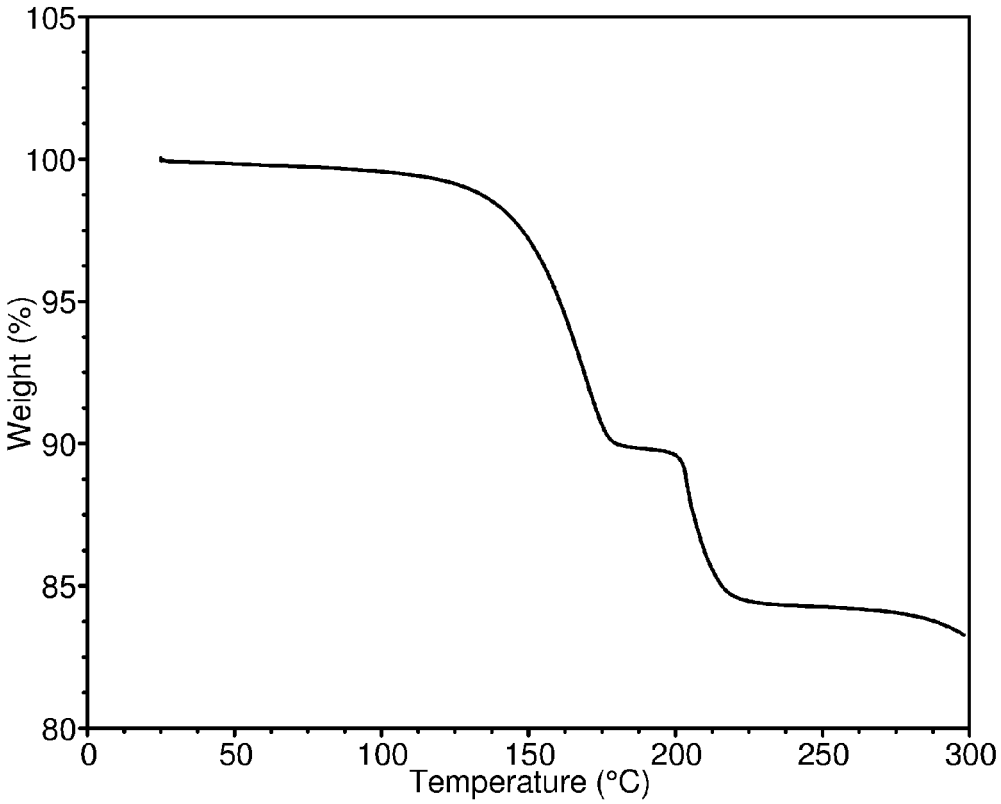
FIG. 3: TGA of N-(cyanomethyl)-4-(2-(4-morpholinophenylamino)pyrimidin-4-yl)benzamide (CYT-0387) dihydrochloride anhydrous Form I.
Figure 4:
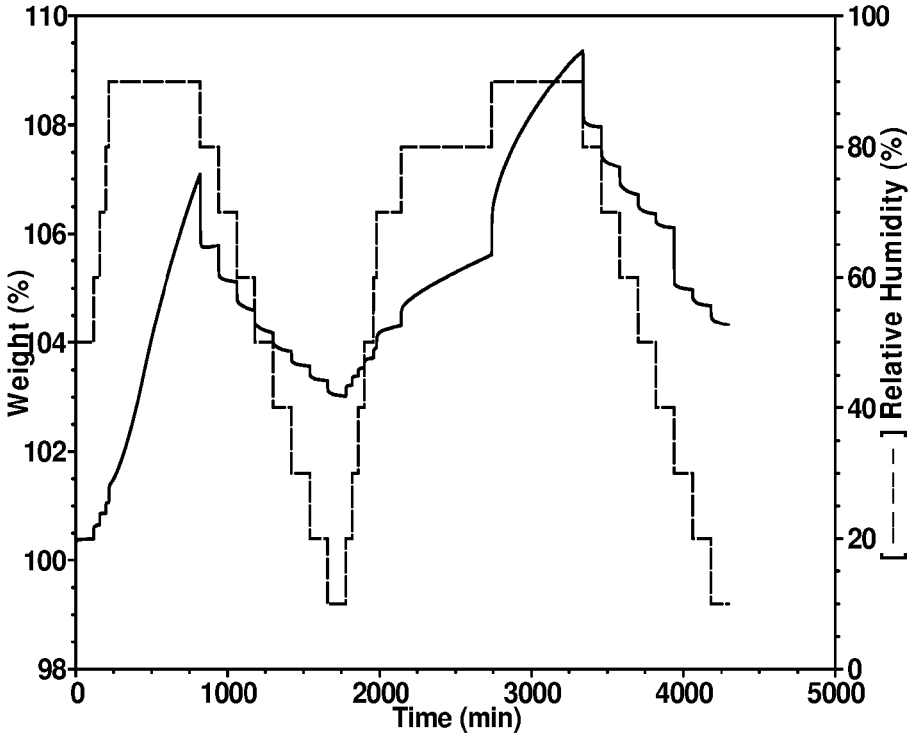
FIG. 4: DVS of N-(cyanomethyl)-4-(2-(4-morpholinophenylamino)pyrimidin-4-yl)benzamide (CYT-0387) dihydrochloride anhydrous Form I.

In certain embodiment, Form IV or CYT-0387 Form IV is characterized by XRPD shown in FIG. 1, DSC in FIG. 2, or TGA in FIG. 3. In one embodiment, Form IV or CYT-0387 Form IV has an XRPD pattern having peaks at about 5.5°, 10.1°, 14.9°, 25.1°, and 26.6° 2−θ±0.2°2−θ.

Results of the present application found that CYT-0387 dihydrochloride monohydrate (Form II) has the increased stability than other salts or forms of CYT-387 at certain conditions. The results described herein also found that such properties of CYT-387 Form II makes it more suitable for developing or adopting to various synthesis or process. In one embodiment, CYT-387 Form II is suitable for use in a pharmaceutical composition in the tablet format. Also, the studies described herein showed the tablet formulation exhibited bioavailability properties similar to those of capsule formulations. In certain embodiments, a tablet comprising CYT-0387 dihydrochloride monohydrate Form II in an amount equivalent to 200 mg of free base of CYT-0387 provides similar bioavailability as a capsule comprising CYT-0387 dihydrochloride anhydrous Form I in an amount equivalent to 300 mg of free base of CYT-0387.

The results of present application indicate that CYT-0387 dihydrochloride anhydrous Form I was hygroscopic and physically unstable when exposed to moisture. Also, the results described below indicate that CYT-0387 dihydrochloride monohydrate Form II is a thermodynamically stable form of the dihydrochloride salt under the conditions suitable for manufacturing and/or storage. In addition, the present application described the use of propyl gallate (a free radical scavenger oxidant) were effective in inhibiting or preventing oxidative degradation of CYT-0387 dihydrochloride monohydrate Form II in an aqueous solution and a tablet formulation. Moreover, the results suggest that CYT-0387 dihydrochloride monohydrate Form II exhibits increased bioavailability compared to CYT-0387 dihydrochloride anhydrous Form I and CYT-0387 free base.

In a still further embodiment, the present invention also provides amorphous N-(cyanomethyl)-4-(2-(4-morpholinophenylamino)pyrimidin-4-yl)benzamide (CYT-0387) dihydrochloride monohydrate. In an additional embodiment, the present invention also provides amorphous N-(cyanomethyl)-4-(2-(4-morpholinophenylamino)pyrimidin-4-yl) benzamide (CYT-0387) monohydrochloride anhydrous and amorphous N-(cyanomethyl)-4-(2-(4-morpholinophenylamino)pyrimidin-4-yl)benzamide (CYT-0387) monohydrochloride anhydrous. In another embodiment, the present invention also provides amorphous N-(cyanomethyl)-4-(2-(4-morpholinophenylamino)pyrimidin-4-yl)benzamide (CYT-0387) dihydrochloride and amorphous N-(cyanomethyl)-4-(2-(4-morpholinophenylamino) pyrimidin-4-yl) benzamide (CYT-0387) monohydrochloride.

In particular embodiments, N-(cyanomethyl)-4-(2-(4-morpholinophenylamino)pyrimidin-4-yl)benzamide (CYT-0387) dihydrochloride monohydrate Form II is in a crystalline form.

In further embodiments, N-(cyanomethyl)-4-(2-(4-morpholinophenylamino)pyrimidin-4-yl)benzamide (CYT-0387) monohydrochloride anhydrous Form I is in a crystalline form.

In certain embodiments, N-(cyanomethyl)-4-(2-(4-morpholinophenylamino)pyrimidin-4-yl)benzamide (CYT-0387) monohydrochloride anhydrous Form III is in a crystalline form.

In one embodiment, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7−0.3, i.e., about 8.4. Depending on the sample preparation techniques, the calibration techniques applied to the instruments, human operational variation, and etc, those skilled in the art recognize that the appropriate error of margins for a XRPD can be ±0.5; ±0.4; ±0.3; ±0.2; ±0.1; ±0.05; or less. In certain embodiments of the invention, the XRPD margin of error is ±0.2.

Additional details of the methods and equipment used for the XRPD analysis are described in the Examples section.

The XRPD peaks for CYT-0387 dihydrochloride anhydrous Form I, CYT-0387, dihydrochloride monohydrate Form II, CYT-0387 monohydrochloride anhydrous Form I and CYT-0387 monohydrochloride anhydrous Form III can be found below in Table 1.

TABLE 1

XRPD peaks for CYT-0387 forms

| CYT-0387 dihydrochloride anhydrous Form I | | CYT-0387, dihydrochloride monohydrate Form II | | CYT-0387 monohydrochloride anhydrous Form I | | CYT-0387 monohydrochloride anhydrous Form III | |
|---|---|---|---|---|---|---|---|
| Position [°2Th.] | Relative Intensity [%] | Position [°2Th.] | Relative Intensity [%] | Position [°2Th.] | Relative Intensity [%] | Position [°2Th.] | Relative Intensity [%] |
| 5.5 | 31.0 | 7.7 | 33.7 | 13.5 | 15.3 | 12.7 | 85.0 |
| 10.1 | 100.0 | 19.3 | 43.7 | 20.9 | 100.0 | 14.6 | 50.0 |
| 14.9 | 66.5 | 24.0 | 100.0 | 26.1 | 20.6 | 17.8 | 55.5 |
| 25.1 | 86.7 | 25.7 | 79.0 | 26.6 | 15.5 | 19.7 | 100.0 |
| 26.6 | 69.3 | 29.6 | 35.7 | 28.3 | 16.6 | 23.3 | 60.1 |

As used herein, the following words, phrases and symbols are generally intended to have the meanings as set forth below, except to the extent that the context in which they are used indicates otherwise.

Reference to "about" a value or parameter herein includes (and describes) embodiments that are directed to that value or parameter per se. For example, description referring to "about X" includes description of "X". In certain embodiments, the term "about" includes the indicated amount±10%. In other embodiments, the term "about" includes the indicated amount±5%. In certain other embodiments, the term "about" includes the indicated amount±1%. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources. If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. "Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

The compounds described herein in which from 1 to n hydrogen atoms attached to a carbon atom may be replaced by a deuterium atom or D, in which n is the number of hydrogen atoms in the molecule. It is known that the deuterium atom is a non-radioactive isotope of the hydrogen atom. Such compounds may increase resistance to metabolism, and thus may be useful for increasing the half-life of the compounds described herein or pharmaceutically acceptable salts, isomers, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium. In some embodiments, the compounds described herein are CYT-0387 dihydrochloride monohydrate Form II, CYT-0387 monohydrochloride anhydrous Form I, CYT-0387 monohydrochloride anhydrous Form III, CYT-0387 dihydrochloride anhydrous Form IV, Compound 3, Compound 4, Compound 8, Compound 10, Compound 12, and Compound 13.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

The terms "Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases or conditions that would benefit from certain treatment; for example, being treated with the compounds according to the present application. The terms "subject in need thereof" or "patient in need thereof" refer to a subject or a patient who may have, is diagnosed, or is suspected to have diseases, or disorders, or conditions that would benefit from the treatment described herein. In certain embodiments, the subject or patient who (i) has not received any treatment, (ii) has received prior treatment and is not responsive or did not exhibit improvement, or (iii) is relapse or resistance to prior treatment.

The term "therapeutically effective amount" of a compound of the present application or a pharmaceutically acceptable salt, isomers, prodrug, or solvate thereof, means an amount sufficient to effect treatment when administered to a subject, to provide a therapeutic benefit such as amelioration of symptoms or slowing of disease progression. The therapeutically effective amount may vary depending on the subject, and disease or condition being treated, the weight and age of the subject, the severity of the disease or condition, and the manner of administering, which can readily be determined by one or ordinary skill in the art. In one embodiment, the therapeutic effective amount of the compound described herein is 100 mg, 150 mg, 200 mg, 250 mg, or 300 mg.

The term "inhibition" indicates a decrease in the baseline activity of a biological activity or process.

Pharmaceutical Compositions and Administration

Compounds provided herein are usually administered in the form of pharmaceutical compositions. Thus, provides herein are also pharmaceutical compositions that contain one or more of the compounds of any of the formulae disclosed herein or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). As used herein, "solvate" is formed by the interaction of a solvent and a compound. Solvates of salts of the compounds of any of the formulae described herein are also provided. Hydrates of the compounds of any of the formulae are also provided. Also, "prodrug" is defined in the pharmaceutical field as a biologically inactive derivative of a drug that upon administration to the human body is converted to the biologically active parent drug according to some chemical or enzymatic pathway.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. Treatment cycles are generally known and are frequently alternated with resting periods of about 1 to 28 days, commonly about 7 days or about 14 days, between cycles. The treatment cycles, in other embodiments, may also be continuous.

In some embodiments, the forms or compositions thereof disclosed herein is formulated for oral administration using pharmaceutically acceptable carriers. Pharmaceutical compositions formulated for oral administration can be in the form of tablets, pills, capsules, cachets, dragees, lozenges, liquids, gels, syrups, slurries, elixirs, suspensions, or powders.

Pharmaceutically Acceptable Carriers

The term "carrier" refers to diluents or fillers, disintegrants, precipitation inhibitors, surfactants, glidants, binders, lubricants, anti-oxidants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

The term "diluent" or "filler" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent. One example of a precipitation inhibitor includes hydroxypropylmethylcellulose.

The term "surfactants" generally refers to compounds that lower the surface tension between two liquids or between a liquid and a solid. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, ethyl cellulose, gelatin, and polyethylene glycol.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

The term "anti-oxidant" generally refers to a substance that inhibits the oxidation of other substances. In certain embodiments of the invention, anti-oxidants are added to the pharmaceutical composition. Examples of anti-oxidants may include ethylenediaminetetraacetic acid, ethylenediaminetetraacetic acid disodium salt, sodium sulfite, sodium metabisulfite, sodium bisulfite, butylated hydroxytoluene (BHT), butylated hydroxyanisole (BHA), ascorbic acid, ascorbyl palmitate, thioglycerol, thioglycolic acid, tocopherol (vitamin E), D-α tocopheryl polyethylene glycol 1000 succinate (vitamin E TPGS) and propyl gallate. In certain embodiment, the antioxidant is propyl gallate. In one embodiment, the pharmaceutical composition comprises CYT-0387 dihydrochloride monohydrate Form II and an antioxidant selected from the group consisting of butylated hydroxyanisole (BHA), ascorbic acid, and propyl gallate. In certain embodiment, the pharmaceutical composition comprises CYT-0387 dihydrochloride monohydrate Form II and an antioxidant, wherein the antioxidant is propyl gallate.

The anti-oxidant or antioxidant may be present in an amount that is sufficient to prevent, inhibit, and/or reduce degradation of the active ingredient (such as CYT-0387 Form II). By way of examples, the antioxidant may be present in an amount of about 0.001%, about 0.002%, about 0.005%, about 0.01%, about 0.02%, about 0.05%, about 0.1%, about 0.2%, about 0.5%, or about 1%. In one embodiment, the pharmaceutical composition comprises propyl gallate at an amount of about 0.001%, about 0.01%, about 0.1%, about 0.2%, about 0.5%, or about 1%. In some embodiment, the pharmaceutical composition comprises CYT-0387 dihydrochloride monohydrate Form II and about 0.2% of propyl gallate.

In certain aspects, provided is a pharmaceutical composition comprising at least one active agent (including, for example, CYT-0387 dihydrochloride monohydrate Form II), and one or more of (a)-(e): a) at least one diluent; b) at least one disintegrant; c) at least one glidant; d) at least one lubricant; and e) at least one anti-oxidant.

In some embodiments, the pharmaceutical composition comprises at least one or at least two diluent(s). In certain embodiments, the pharmaceutical composition comprises one or two diluent(s). In certain embodiments, the diluent is selected from the group consisting of mannitol, microcrystalline cellulose, lactose, dextrose, sucrose, ludiflash, F-melt, advantose, GalenIQ, or any mixtures thereof. In one embodiment, the diluent is mannitol, microcrystalline cellulose, or a mixture thereof.

In some embodiments, the pharmaceutical composition comprises at least one disintegrant. In certain embodiments, the pharmaceutical composition comprises one disintegrant. In a particular embodiment, the disintegrant is sodium starch glycolate. In one embodiment, the disintegrant is croscarmellose sodium. In another embodiment, the disintegrant is crospovidone.

In some embodiments, the pharmaceutical composition comprises at least one glidant. In certain embodiments, the pharmaceutical composition comprises one glidant. In one embodiment, the glidant is colloidal silicon dioxide.

In some embodiments, the pharmaceutical composition comprises at least one lubricant. In certain embodiments, the pharmaceutical composition comprises one lubricant. In one embodiment, the lubricant is magnesium stereate.

In particular embodiments, the pharmaceutical composition comprises CYT-0387 dihydrochloride monohydrate Form II, at least one diluent, at least one disintegrant, at least one glidant, at least one lubricant, and at least one antioxidant. In further embodiments, the at least one diluent is microcrystalline cellulose, the at least one disintegrant is sodium starch glycolate, the at least one glidant is colloidal silicon dioxide, the at least one lubricant is magnesium stearate, and at least one anti-oxidant is propyl gallate. In yet further embodiments, the at least one diluent is lactose, the at least one disintegrant is sodium starch glycolate, the at least one glidant is colloidal silicon dioxide, the at least one lubricant is magnesium stearate, and at least one antioxidant is propyl gallate.

In other embodiments, the pharmaceutical composition comprises CYT-0387 dihydrochloride monohydrate Form II, at least two diluents, at least one disintegrant, at least one glidant, at least one lubricant, and at least one anti-oxidant. In yet other embodiments, the at least two diluents are microcrystalline cellulose and lactose, the at least one disintegrant is sodium starch glycolate, the at least one glidant is colloidal silicon dioxide, the at least one lubricant is magnesium stearate, and at least one anti-oxidant is propyl gallate.

In certain embodiments, the pharmaceutical composition comprises CYT-0387 of which at least about 80% is CYT-0387 dihydrochloride monohydrate Form II. In further embodiments, the pharmaceutical composition comprises CYT-0387 of which at least about 85% is CYT-0387 dihydrochloride monohydrate Form II. In still further embodiments, the pharmaceutical composition comprises CYT-0387 of which at least about 90% is CYT-0387 dihydrochloride monohydrate Form II. In yet further embodiments, the pharmaceutical composition comprises CYT-0387 of which at least about 95% is CYT-0387 dihydrochloride monohydrate Form II. In particular embodiments, the pharmaceutical composition comprises CYT-0387 of which at least about 97% is CYT-0387 dihydrochloride monohydrate Form II. In other embodiments, the pharmaceutical composition comprises CYT-0387 of which at least about 98% is CYT-0387 dihydrochloride monohydrate Form II. In still other embodiments, the pharmaceutical composition comprises CYT-0387 of which at least about 99% is CYT-0387 dihydrochloride monohydrate Form II. In yet other embodiments, the pharmaceutical composition comprises CYT-0387 of which at least about 99.5% is CYT-0387 dihydrochloride monohydrate Form II. In particular embodiments, the pharmaceutical composition comprises CYT-0387 of which at least about 99.9% is CYT-0387 dihydrochloride monohydrate Form II.

It should be understood that the pharmaceutical composition comprises pharmaceutically acceptable carriers detailed herein, the same as if each and every combination of pharmaceutically acceptable carrier were specifically and individually listed.

Unit Dosage Forms

In some embodiments, the pharmaceutical compositions as described herein are formulated in a unit dosage form. The term "unit dosage forms" refers to physically discrete units suitable as unitary dosages for subjects (e.g., human subjects and other mammals), each unit containing a predetermined quantity of active material calculated to produce the desired therapeutic effect, in association with a suitable pharmaceutical carrier.

In a further embodiment, the invention is directed to unit dosage forms comprising CYT-0387 dihydrochloride monohydrate Form II. In some embodiments, the unit dosage form comprises CYT-0387 dihydrochloride monohydrate Form II in amount equivalent to from about 10 mg to about 1000 mg, about 10 mg to about 800 mg, about 10 mg to about 700 mg about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 1000 mg, about 50 mg to about 800 mg, about 50 mg to about 700 mg about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 1000 mgs, about 100 mg to about 800 mg, about 100 mg to about 700 mg about 100 mg to about 500 mg, about 100 mg to about 400 mg, about 100 mg to about 300 mg, about 100 mg to about 250 mg, about 100 mg to about 200 mg, about 150 mg to about 300 mg, about 150 mg to about 250 mg, about 150 mg to about 200 mg, about 200 mg to about 300 mg, about 200 mg to about 250 mg, or about 200 mg to about 300 mg of CYT-0387 free base.

In additional embodiments, the dosage form comprises CYT-0387 dihydrochloride monohydrate Form II in an amount equivalent to about 100 mg of CYT-0387 free base, about 150 mg CYT-0387 free base, 200 mg of CYT-0387 free base, about 250 mg CYT-0387 free base, 300 mg of CYT-0387 free base, about 400 mg CYT-0387 free base, or about 500 mg of CYT-0387 free base. In certain embodiments, the unit dosage form comprises CYT-0387 dihydrochloride monohydrate Form II in an amount equivalent to about 50 mg of CYT-0387 free base. In other embodiments, the unit dosage form comprises CYT-0387 dihydrochloride monohydrate Form II in an amount equivalent to about 100 mg of CYT-0387 free base. In yet other embodiments, the unit dosage form comprises CYT-0387 dihydrochloride monohydrate Form II in an amount equivalent to about 150 mg of CYT-0387 free base. In still other embodiments, the dosage form comprises CYT-0387 dihydrochloride monohydrate Form II in an amount equivalent to about 200 mg of CYT-0387 free base. In particular embodiments, the dosage form comprises CYT-0387 dihydrochloride monohydrate Form II in an amount equivalent to about 250 mg of CYT-0387 free base. In further embodiments, the dosage form comprises CYT-0387 dihydrochloride monohydrate Form II in an amount equivalent to about 300 mg of CYT-0387 free base. In yet further embodiments, the dosage form comprises CYT-0387 dihydrochloride monohydrate Form II in an amount equivalent to about 400 mg of CYT-0387 free base. In still further embodiments, the dosage form comprises CYT-0387 dihydrochloride monohydrate Form II in an amount equivalent to about 500 mg of CYT-0387 free base. In other embodiments, the pharmaceutical composition is a tablet at a dosage form comprising CYT-0387 dihydrochloride monohydrate Form II in an amount equivalent to about 300 mg of CYT-0387 free base.

In further embodiments, the invention is directed to dosage forms comprising CYT-0387 dihydrochloride monohydrate Form II in an amount equivalent to 200 mg of the free base N-(cyanomethyl)-4-(2-(4-morpholinophenylamino)pyrimidin-4-yl)benzamide which provide a pharmacokinetic profile substantially similar to a dosage form comprising CYT-0387 dihydrochloride anhydrous Form I in an amount equivalent to 300 mg of the free base N-(cyanomethyl)-4-(2-(4-morpholinophenylamino)pyrimidin-4-yl)benzamide.

In certain embodiments of the invention, the unit dosage form comprises at least one pharmaceutically acceptable carrier. In other embodiments, the unit dosage form comprises CYT-0387 dihydrochloride monohydrate Form II, at least two diluents, at least one disintegrant, at least one glidant, at least one lubricant, and at least one anti-oxidant. In still further embodiments, the unit dosage form comprises about 36% to 44% CYT-0387 dihydrochloride monohydrate Form II; about 44% to 58% diluent; about 4% to 8% disintegrant, about 0.25% to 0.75% glidant, about 1.2% to 1.8% lubricant, and about 0.1% to 0.5% anti-oxidant. In yet other embodiments, the at least two diluents are microcrystalline cellulose and lactose, the at least one disintegrant is sodium starch glycolate, the at least one glidant is colloidal silicon dioxide, the at least one lubricant is magnesium stearate, and at least one anti-oxidant is propyl gallate. In still further embodiments, the unit dosage form comprises about 36% to 44% CYT-0387 dihydrochloride monohydrate Form II; about 30% to 38% microcrystalline cellulose; about 14% to 20% lactose, about 4% to 8% sodium starch glycolate, about 0.25% to 0.75% colloidal silicon dioxide, about 1.2% to 1.8% magnesium stearate, and about 0.1% to 0.5% propyl gallate.

Manufacturing of Pharmaceutical Compositions

The pharmaceutical compositions described herein can be manufactured using any conventional method, such as, but not limited to, mixing, dissolving, granulating, dragee-making, levigating, emulsifying, encapsulating, entrapping, melt-spinning, spray-drying, or lyophilizing processes.

A skilled artisan would recognize suitable methods and techniques to prepare a tablet by conventional formulation. Exemplary methods and techniques to prepare powders for compression into a tablet include dry granulation or wet granulation. Dry granulation generally refers to the process of forming granules without using a liquid solution, whereas wet granulation generally refers to the process of adding a liquid solution to powders to granulate.

Kits

Provided herein are also kits that include a compound of the formulae of the present application or a pharmaceutically acceptable salt, isomer, prodrug, or solvate thereof, and suitable packaging. In one embodiment, a kit further includes instructions for use. In one aspect, a kit includes a compound of the formulae described herein or a pharmaceutically acceptable salt, isomer, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, isomer, prodrug, or solvate thereof, in a suitable container. The container may be a vial, jar ampoule, preloaded syringe, and intravenous bag.

Methods of Treatment

The CYT-0387 forms of the present invention may be used in the treatment of kinase associated diseases including JAK kinase associated diseases such as immunological and inflammatory diseases including organ transplants; hyperproliferative diseases including cancer and myeloproliferative diseases; viral diseases; metabolic diseases; and vascular diseases.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The terms "treating" or "treatment" refer to obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. Treatment may cover any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent may be administered before, during or after the onset of disease. The treatment of ongoing disease, where the treatment stabilizes or reduces the undesirable clinical symptoms of the patient, is of particular interest. The expected progression-free survival times can be measured in months to years, depending on prognostic factors including the number of relapses, stage of disease, and other factors. Prolonging survival includes without limitation times of at least 1 month, about at least 2 months, about at least 3 months, about at least 4 months, about at least 6 months, about at least 1 year, about at least 2 years, about at least 3 years, or more. Overall survival can also be measured in months to years. The patient's symptoms may remain static or may decrease.

The term "effective amount" refers to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts.

The term "kinase associated diseases" refers to a disorder or disorders that directly or indirectly result from or are aggravated by aberrant kinase activity, in particular JAK activity and/or which are alleviated by inhibition of one or more of these kinase enzymes.

In a preferred embodiment the kinase associated disease state involves one or more of the JAK kinases, JAK1, JAK2, JAK3 or TYK2. In a particularly preferred embodiment, the disease involves JAK2 kinase. Such diseases include, but are not limited to, those listed in the Table below.

Activation of the JAK/STAT Pathway in Various Pathologies

| Disease Type | Cell Types Involved | Cytokines involved | JAK Kinase Involved | Characteristics |
|---|---|---|---|---|
| Atopy | | | | |
| Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |
| CMI | | | | |
| Allergic Contact Dermatitis, hypersensitivity pneumonitis | T-cells, B-cells, macrophages, Neutrophils | IL-2, IL-4, IL-5, IL-6, IL-10, IFNγ, TNF, IL-7, IL-13, | JAK1, JAK2, JAK3, Tyk2 | B cell and/or $T_{DH}$ cell activation Macrophage/granulocyte activation |
| AutoImmune Diseases | | | | |
| Multiple sclerosis, Glomerulonephritis Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis | B-Cells, T cells, monocytes, Macrophages, Neutrophils, Mast Cells, Eosinophils, | IL-2, IL-4, IL-5, IL-6, IL-7, Il-10, IL-13, IFNγ, TNF, GM-CSF; G-CSF, | JAK1, JAK2, JAK3, Tyk2 | Cytokine Production (e.g. TNFα/β, IL-1, CSF-1, GM-CSF), T-cell Activation, B cell activation, JAK/STAT activation |
| Transplantation | | | | |
| Allograft Rejection GvHD | T cells, B cells, Macrophages | IL-2, IL-4, IL-5, IL-7, IL-13, TNF | JAK1, JAK2, JAK3, | Macrophage/T cell mediated necrosis, Tc cell mediated apoptosis, and B cell/Ig mediated opsonization/necrosis of foreign graft |
| Viral Diseases | | | | |
| Epstein Barr Virus (EBV) | Lymphocytes | Viral Cytokines, IL-2, | JAK1, JAK2, JAK3 | JAK/STAT Mediation |
| Hepatitis B | Hepatocytes | | | |
| Hepatitis C | Hepatocytes | | | |
| HIV | Lymphocytes | | | |
| HTLV 1 | Lymphocytes | | | |
| Varicella-Zoster Virus (VZV) | Fibroblasts | | | |
| Human Papilloma Virus (HPV) | Epithelial cells | | | |
| Hyperproliferative diseases-cancer | | | | |
| Leukemia | Leucocytes | Various Autocrine cytokines, Intrinsic Activation | JAK1, JAK2, JAK3 | Cytokine production, JAK/STAT Activation |
| Lymphoma | Lymphocytes | | | |
| Multiple Myeloma | Various | | | |
| prostate cancer | Various | | | |
| breast cancer | Various | | | |
| hodgkins lympohoma | Various | | | |
| B-cell chronic lymphocytic leukemia | Various | | | |
| lung cancer | Various | | | |
| hepatoma | Various | | | |
| metastatic melanoma | Various | | | |
| glioma | Various | | | |

-continued

| Activation of the JAK/STAT Pathway in Various Pathologies | | | | |
|---|---|---|---|---|
| Disease Type | Cell Types Involved | Cytokines involved | JAK Kinase Involved | Characteristics |
| Myeloproliferative Diseases | | | | |
| Polycythemia vera (PV), primary myelofibrosis, thrombocythemia, essential thrombocythemia (ET), idiopathic myelofibrosis, chronic myelogenous leukemia, systemic mastocystosis (SM), chronic neutrophilic leukemia (CNL), myelodisplastic syndrome (MDS), systemic mast cell disease (SMCD) | Hematopoietic | Interleukin-3, erythropoietin, thrombopoietin | JAK2 mutation | JAK/STAT activation |
| Vascular Disease | | | | |
| Hypertension, Hypertrophy, Heart Failure, Ischemia, Pulmonary arterial hypertension | Endothelial cells, smooth muscle cells including pulmonary artery smooth muscle cells, cardiac myocytes, fibroblasts, endothelial cells | IL6, angiotensin II, LIF, TNFalpha, serotonin, caveolin 1 | JAK1, JAK2, TYK2 | JAK/STAT activation |
| Metabolic disease | | | | |
| Obesity, metabolic syndrome | Adipocytes, pituitary cells, neurons, Monocytes | Leptin | JAK2 | JAK/STAT activation |

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease, cystic fibrosis, inflammatory bowl disease, irritable bowl syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Motor Neurone Disease (Lou Gehrig's disease), Paget's disease, sepsis, conjunctivitis, neranl catarrh, chronic arthrorheumatism, systemic inflammatory response syndrome (SIRS), polymyositis, dermatomyositis (DM), Polaritis nodoa (PN), mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostrate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfronna (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma]), fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphoma; Skin: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myeloproliferative diseases such as polycythemia vera (PV), primary myelofibrosis, thrombocythemia, essential thrombocythemia (ET), agnoneic myeloid metaplasia (AMM), also referred to as idiopathic myelofibrosis (IMF), chronic myelogenous leukemia (CML), systemic mastocystosis (SM), chronic neutrophilic leukemia (CNL), myelodisplastic syndrome (MDS) and systemic mast cell disease (SMCD). In certain embodiment, the myelofibrosis disease is selected from polycythemia vera (PV), primary myelofibrosis, thrombocythemia, and essential thrombocythemia (ET). In one embodiment, the pharmaceutical composition of the present application may be suitable for treating myeloproliferative diseases, wherein the myelofibrosis disease is selected from polycythemia vera (PV), primary myelofibrosis, thrombocythemia, and essential thrombocythemia (ET). In some embodiment, the pharmaceutical composition of the present application may be suitable for treating primary myelofibrosis.

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

Preferred diseases for JAK2 selective inhibitors include immunological and inflammatory diseases such as autoimmune diseases for example atopic dermatitis, asthma, rheumatoid arthritis, Crohn's disease, psoriasis, Crouzon syndrome, achondroplasia, systemic lupus erythematosus, scleroderma, mixed connective tissue disease, vasculitis, thanatophoric dysplasia and diabetes; hyperproliferative disorders such as cancer for example prostate cancer, colon cancer, breast cancer, liver cancer such as hepatoma, lung cancer, head and neck cancer such as glioma, skin cancer such as metastatic melanoma, leukemia, lymphoma, multiple myeloma and myeloproliferative diseases such as polycythemia vera (PV), myelofibrosis, thrombocythemia, essential thrombocythemia (ET), agnoneic myeloid metaplasia (AMM), also referred to as idiopathic myelofibrosis (IMF) and chronic myelogenous leukemia (CML); and vascular diseases such as hypertension, hypertrophy, stroke, Raynaud's phenomenon, POEMS syndrome, angina, ischemia, migraine, peripheral arterial disease, heart failure, restenosis, atherosclerosis and pulmonary arterial hypertension.

In other embodiments, the disease is a solid tumor. By way of examples, the solid tumor includes but is not limited to pancreatic cancer, bladder cancer, colorectal cancer, breast cancer, prostate cancer, renal cancer, hepatocellular cancer, lung cancer, ovarian cancer, cervical cancer, rectum cancer, liver cancer, kidney cancer, stomach cancer, skin cancer, gastric cancer, esophageal cancer, head and neck cancer, melanoma, neuroendocrine cancers, CNS cancers (e.g., neuroblastoma), brain tumors (e.g., glioma, anaplastic oligodendroglioma, adult glioblastoma multiforme, and adult anaplastic astrocytoma), bone cancer, or soft tissue sarcoma. In some embodiments, the solid tumor is non-small cell lung cancer, small-cell lung cancer, colon cancer, CNS cancer, melanoma, ovarian cancer, renal cancer, pancreatic cancer, prostate cancer, or breast cancer. In particular embodiments, the solid tumor is non-small cell lung cancer, colon cancer, pancreatic cancer, or breast cancer. In further embodiments, the solid tumor is non-small cell lung cancer. In still further embodiments, the solid tumor is colon cancer. In yet further embodiments, the solid tumor is pancreatic cancer. In even further embodiments, the solid tumor is breast cancer.

In further methods of the present invention, CYT-0387, or a form thereof, including CYT-0387 dihydrochloride monohydrate Form II, is used to maintain or elevate hemoglobin levels in a subject experiencing anemia or a hemoglobin decline. Anemic subjects have an endogenous hemoglobin level that is lower than the level that is normal for healthy subject of equivalent age and gender. Acceptable or "normal" levels are now well established in medical practice. For an adult human male, anemia is evident when the hemoglobin level is below about 13.0 g/dL; for non-pregnant adult human females, deficiency is evident when the hemoglobin level is below about 12.0 g/dL. Measurement of hemoglobin levels is performed using well established techniques. Conditions of severe anemia are evident when the hemoglobin level is less than about 8.0 g/dL.

In use, CYT-0387 is administered to an anemic subject in an amount effective to maintain or elevate the level of hemoglobin in the subject. Administration of the drug thus has the minimum effect of inhibiting further reduction in the level of hemoglobin in the treated subject. More desirably, administration of the drug has the effect of increasing the level of hemoglobin in the subject.

Anemic subjects that would benefit from treatment with CYT-0387 include subjects that have undergone or are undergoing chemotherapy or radiation therapy, such as cancer patients. A wide variety of chemotherapeutic agents are known to have the consequence of reducing the level of functioning red blood cells. As well, subjects that are CYT-0387 treatment candidates are those afflicted with blood disorders including blood cancers that result in, or are associated with, a reduction in red blood cell count. In embodiments, the subjects to be treated are subjects having anemia associated with or resulting from such blood conditions as myelodysplastic syndrome. Myelodysplasia syndromes (MDS) is a term used to describe a group of diseases characterized by ineffective hematopoiesis leading to blood cytopenias and hypercellular bone marrow. MDS has traditionally been considered to be synonymous with 'preleukemia' because of the increased risk of transformation into acute myelogenous leukemia (AML). Evolution to AML and the clinical consequences of cytopenias are main causes of morbidity and mortality in MDS. Debilitating symptoms of MDS include fatigue, pallor, infection, and bleeding. Anemia, neutropenia, and thrombocytopenia are also common clinical manifestations of MDS. In other embodiments, the subjects to be treated are subjects having anemia associated with or resulting from such other blood conditions as anemias associated with other hematologic malignancies, aplastic anemia, anemia of chronic disease that affect red blood cells and the like. Anemia of chronic disease is associated with such diseases as certain cancers including lymphomas and Hodgkin's disease; autoimmune diseases such as rheumatoid arthritis, systemic lupus erythematosis, inflammatory bowel disease and polymyalgia rheumatica; long term infections such as urinary tract infection, HIV and osteomyelitis; heart failure; and chronic kidney disease. In addition, patients with anemia resulting from conditions associated with increased destruction, shortened red blood cell survival and splenic sequestration could also benefit from CYT-0387 treatment. Patients afflicted with these conditions thus can be treated to improve upon their state of declining or deficient hemoglobin.

In certain embodiments, the subject to be treated is an anemic subject experiencing thalassemia. In other embodiments, the subject to be treated is a subject other than a subject experiencing thalassemia.

In embodiments, a CYT-0387 form of the present invention, such as CYT-0387 dihydrochloride monohydrate Form II, is administered to a subject diagnosed with a myeloproliferative disease such as myeloproliferative neoplasm, thereby to improve upon the prognosis of the disease and, in embodiments, particularly to treat hemoglobin deficiency or decline associated with the disease. In other embodiments, a CYT-0387 form of the present invention, such as CYT-0387 dihydrochloride monohydrate Form II, is administered to an anemic subject that is other than an anemic subject diagnosed with a myeloproliferative disease. This class of treatable subject presents with anemia unrelated to myeloproliferative disease. In some embodiments, a CYT-0387 form of the present application, such as CYT-0387 dihydrochloride monohydrate Form II, is administered to an anemic subject that is diagnosed with cancer.

"Myeloproliferative diseases" and "myeloproliferative neoplasms (MPN)" most notably polycythemia vera (PV), essential thrombocythemia (ET) and primary myelofibrosis (PMF) are a diverse but inter-related group of clonal disorders of pluripotent hematopoietic stem cells that share a range of biological, pathological and clinical features including the relative overproduction of one or more cells of myeloid origin, growth factor independent colony formation in vitro, marrow hypercellularity, extramedullary hematopoiesis, spleno- and hepatomegaly, and thrombotic and/or hemorrhagic diathesis. An international working group for myeloproliferative neoplasms research and treatment (IWG-MRT) has been established to delineate and define these conditions (see for instance Vannucchi et al, CA Cancer J. Clin., 2009, 59: 171-191), and those disease definitions are to be applied for purposes of this specification. Subjects, most notably human patients, who present with MPN and particularly PMF are identifiable in the art using the IWG-MRT criteria mentioned above. Subjects "at risk for" a particular form of MPN are subjects having an early stage form of the disease, and may for instance include subjects having a genetic marker thereof, such as the JAK2V617F allele which is associated with PV (>95%), with ET (60%) and with PMF (60%). Subjects are also considered to be "at risk for" a form of MFN if they already manifest symptoms of an earlier stage form. Thus, subjects presenting with MFN are at risk for post-PV and post-ET, both of which develop following MPN.

The response of MPN patients and particularly PMF patients to CYT-0387 therapy is particularly robust when, according to the present invention, they are patients selected for CYT-0387 therapy based on one or more of the following i. prior therapy with a drug selected from thalidomide, lenalidomide, pomalidomide and a JAK2 inhibitor other than CYT-0387;

ii. a clinical criterion selected from one or both of (1) smaller spleen size and (2) a lower percentage of circulating blasts;

iii. a biochemical marker criterion selected from one or more of (1) an increased level of at least one protein selected from EGF, TNF-α, G-CSF, IFN-α, MIP-β, HGF, MIG, and VEGF; (2) a decreased level of eotaxin; and (3) an altered level of at least one protein selected from EPO, hepcidin and BMP-2.

The improved outcome from CYT-0387 therapy that results from prior patient selection is manifested as a robust improvement in anemia response and/or in spleen response. By "anemia response" is meant an increase in the patient's hemoglobin level or a patient who was transfusion dependent becoming transfusion independent. Desirably, a minimum increase in hemoglobin of 2.0 g/dL lasting a minimum of 8 weeks is achieved, which is the level of improvement specified in the International Working Group (IWG) consensus criteria. However, smaller, but still medically significant, increases in hemoglobin are also considered to be within the term "anemia response".

By "spleen response" is meant a reduction in the size of the patient's spleen as assessed by either palpation of a previously palpable spleen during physical exam or by diagnostic imaging. The IWG consensus criteria specifies that there be either a minimum 50% reduction in palpable splenomegaly (spleen enlargement) of a spleen that is at least 10 cm at baseline (prior to treatment) or of a spleen that is palpable at more than 5 cm at baseline becomes not palpable. However, smaller reductions are also considered to be within the term "spleen response".

In one embodiment, the selected patient is one that has received prior drug therapy. More particularly, patients selected for CYT-0387 therapy include patients that have been treated, or are currently being treated, with thalidomide (CAS number 50-35-1) or with a derivative thereof, particularly lenalidomide (CAS number 191732-72-6). These drugs are both used in the treatment of multiple myeloma, and appear also to be showing some benefit in patients afflicted with myeloproliferative disorder. To receive the further benefit resulting from subsequent CYT-0387 therapy, patients will either be undergoing treatment with thalidomide, lenalidomide or pomalidomide or similar agent or will have been treated with one of these drugs within a time frame, relative to CYT-0387 therapy onset, sufficient for the effects of these drugs to be manifest Patients meeting these criteria experience significant anemia response, relative to patients naive to this drug therapy, when subsequently treated with CYT-0387. In a preferred embodiment, the CYT-0387 patient is one subjected to prior therapy with lenalidomide.

Patients selected for CYT-0387 therapy also include patients that have been treated, or are undergoing treatment, with a JAK inhibitor other than CYT-0387. It has been found in particular that patients previously treated with the JAK inhibitor designated INCBO 18424, or the JAK inhibitor designated TG101348, have a more prominent spleen response to CYT-0387 therapy than patients naive to such prior therapy. In a preferred embodiment, the patient selected for CYT-0387 therapy is one that, in addition to being subjected to therapy with a JAK inhibitor other than CYT-0387, is also a transfusion dependent patient. INCBO 18424 is administered at starting doses of 15 or 20 mg po BID with dose titration from 5 mg BID to 25 mg BID. TG101348 is administered once a day with a maximum tolerated dose (MTD) determined to be 680 mg/day. JAK inhibitors other than CYT-0387 include all and any other JAK inhibitors, and particularly other JAK inhibitors having a JAK affinity, selectivity or binding site different from CYT-0387. These properties can be determined using the JAK2 crystal structure and the modeling approach and activity assays described in U.S. Pat. No. 7,593,820, the entire disclosure of which is incorporated herein by reference. To receive the further benefit resulting from subsequent CYT-0387 therapy, patients will either be undergoing treatment with the other JAK2 inhibitor or will have been treated with such a drug within a time frame, relative to CYT-0387 therapy onset, sufficient for the effects of that JA 2 inhibitor to be manifest in the patient.

Patients selected for CYT-0387 therapy also include patients having altered levels of detectable protein markers. More particularly, patients in whom the levels of certain protein markers, including certain cytokines and chemokines, are elevated can experience significant benefit when treated with CYT-0387, in terms of their anemia response and/or their spleen response to CYT-0387 therapy. In embodiments, elevation in the level of one or more of the following protein markers signifies that the patient is a preferred candidate for CYT-0387 therapy:

(1) EGF, or epidermal growth factor, the mature form of which comprises residues 971-1023 of the sequence having Swiss-Prot designation P01133;

(2) TNF-a, or tumour necrosis factor alpha, the mature and soluble form of which comprises residues 77-233 of the sequence having Swiss-Prot designation P01375;

(3) G-CSF, or granulocyte colony stimulating factor, the mature form of which comprises residues 30-207 of the sequence having Swiss-Prot designation P09919;

(4) IFN-α, or interferon alpha, comprises a family of subtypes the mature forms of which are well known in the art;

(5) MIP-Iβ, or macrophage inflammatory protein 1-beta (now known also as C—C motif chemokine 4, or CCL4), the mature form which comprises either residues 24-92 or 26-92 of the sequence having Swiss-Prot designation PI 3236;

(6) HGF, or hepatocyte growth factor, the mature forms of which are based on the sequence having Swiss-Prot designation P14210, and include the alpha chain having residues 32-494 and the beta chain having residues 495-728;

(7) MIG, or monokine induced by gamma interferon (now known also as CXCL9), is within the family of chemotactic cytokines, the mature form of which comprises residues 23-125 of the sequence having Swiss-Prot designation Q07325;

(8) VEGF, or vascular endothelial growth factor A, the mature form of which comprises residues 27-232 of the sequence having Swiss-Prot designation PI 5692.

Patients presenting for CYT-0387 therapy experience a significant spleen response when they are selected initially based on an elevation in the level of any one or more of the markers noted above. An elevated level is a level that is greater than the level in a normal subject.

Patients presenting for CYT-0387 therapy can also experience a significant anemia response when they are selected initially based on a depression in the level of the protein eotaxin. This protein, known also as eosinophil chemotatic protein and comprising residues 24-97 of the sequence having Swiss-Prot designation P51671, functions through interaction with CC 3 to promote accumulation of esoinophils in response to allergens, a prominent feature of allergic inflammatory reactions.

Still other markers useful to select patients for CYT-0387 therapy include altered levels of EPO, hepcidin and BMP-2. Another example of markers useful to select patients for CYT-0387 therapy includes the levels of BMP-6.

Other markers may be used in monitoring CYT-0387 therapy or dosing regimen. By way of example, such markers may include but are not limited to Compound 3, Compound 4, Compound 8, Compound 10, Compound 12, and Compound 13. The levels of these markers may be detected by the methods that are commonly used, such as those described in the examples of the present application.

The "level" of a given marker is considered to be altered, i.e., either elevated or reduced, when the level measured in a given patient is different to a statistically significant extent from the corresponding level in a normal subject. Patients that present with marker levels altered to an extent sufficient, desirably, to yield a p value of at least 0.05 or more significant, i.e., better, are selected as candidates for CYT-0387 therapy. In embodiments, the p value is at least 0.03, 0.02 or 0.01, and in preferred embodiments the p value is at least 0.009, 0.007, 0.005, 0.003, 0.001 or better.

The levels of a given marker can be determined using assays already well established for detection the markers noted above. In embodiments, this is achieved by extracting a biological sample from the patient candidate, such as a sample of whole blood or a fraction thereof such as plasma or serum. The sample then is treated to enrich for the marker of interest, if desired, and the enriched or neat sample is assayed for instance using a detectable ligand for the marker, such as a labeled antibody that binds selectively to the marker. The amount of marker present in the sample can then be determined either semi-quantitatively or quantitatively, to obtain a value that is then compared against a reference value that is the normal level for that marker in a healthy subject. As noted above, a difference in marker levels sufficient to arrive at a p value that is at least 0.05 indicates an altered marker level of significance, and patients presenting with an elevated level of that marker (or in the case of eotaxin, a decreased level) are candidates for CYT-0387 therapy.

Also suitable as candidates for CYT-0387 therapy are those patients that meet certain clinical criteria, including those presenting with a spleen of relatively small size, and those presenting with an elevated level of circulating, or peripheral, blasts. These patients respond to CYT-0387 therapy particularly well, in terms of their spleen response. In one embodiment, the selected patient is one that has not yet progressed to transfusion dependency. Splenic enlargement is assessed by palpation. Splenic size and volume can also be measured by diagnostic imaging such as ultrasound, CT or MRI). Normal spleen size is approximately 11.0 cm. in craniocaudal length.

Also suitable as candidates for CYT-0387 therapy are those patients presenting with a lower percentage of circulating blasts. Blasts are immature precursor cells that are normally found in the bone marrow and not the peripheral blood. They normally give rise to mature blood cells. The lower percentage of circulating blasts is measured by cytomorphologic analysis of a peripheral blood smear as well as multiparameter flow cytometry and immunohistochemistry. As a prognostic factor >1=1% blasts is used.

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

In one embodiment, the application provides a formulation described herein and an additional therapeutic agent as a combined preparation for simultaneous, separate or sequential use in therapy, e.g. a method of treating a disease, disorder, or condition that is mediated by JAK. The therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof. In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Auroa kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or CK2) inhibitor, a DDR (discoidin domain receptor, including DDR1 and/or DDR2) inhibitor, a EGFR inhibitor, a FXR (farnesoidxreceptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (1-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXLS) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L1 (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2, TLR-3, TLR-4, TLR-5, TLR-6, TLR-7, TLR-8, TLR-9, TLR-10, TLR-11, TLR-12, and/or TLR-13) inhibitor, a TK (tyrosine kinase) inhibitor, a TPL2 (serine/threonine kinase) inhibitor, a NEK9 inhibitor, an Ab1 inhibitor, a p38 kinase inhibitor, a PYK inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the PI3K-δ inhibitor is (S)-2-(1-((9H-purin-6-yl)amino)propyl)-5-fluoro-3-phenylquinazolin-4(3H)-one as named by ChemDraw (may also be referred to as 5-Fluoro-3-phenyl-2-[(1S)-1-(9H-purin-6-ylamino)propyl] quinazolin-4(3H)-one) and may be synthesized by the methods described in U.S. Pat. No. 7,932,260. In certain embodiment, the SyK inhibitor is 6-(1H-indazol-6-yl)-N-(4-morpholinophenyl)imidazo[1,2-a]pyrazin-8-amine as named by ChemDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amino-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, tenipo side); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, Pseudomonas exotoxin, Bordetella pertussis adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL® and docetaxel (TAXOTERE®); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace(r)), exemestane, formestane, fadrozole, vorozole (Rivisor(r)), letrozole (Femara(r))), and anastrozole (Arimidex(r)); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r)), suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, betaaminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1 -anti-collagenase-serum, alpha-2-antiplasmin, bisantrene, lobenzarit disodium, n-2-carboxyphenyl-4-chloroanthronilic acid disodium or "CCA", thalidomide; angiostatic steroid, carg-boxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. Nos. 5,021,456; 5,5059,714; 5,120,764; 5,182,297; 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, obinutuzumab, CC49 and 3F8. The exemplified therapeutic antibodies may be further labeled or combined with a radioisotope particle, such as indium In 111, yttrium Y 90, iodine 1-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" The New England Journal of Medicine 2008, 359(6), p. 613-626; and Wierda, W. G., "Current and Investigational Therapies for Patients with CLL" Hematology 2006, p. 285-294. Lymphoma incidence patterns in the United States is profiled in Morton, L. M., et al. "Lymphoma Incidence Patterns by WHO Subtype in the United States, 1992-2001" Blood 2006, 107(1), p. 265-276.

Examples of immunotherapeutic agents include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DRS antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents include aldesleukin, alvocidib, antineoplaston AS2-1, antineoplaston A10, antithymocyte globulin, amifostine trihydrate, aminocamptothecin, arsenic trioxide, beta alethine, Bcl-2 family protein inhibitor ABT-263, ABT-199, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine 1-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

It is understood that the below examples illustrate certain aspects of the present application. It is also understood that values and parameters shown in the examples may be modified within reasonable variation, and that various modifications may be made within the scope of the present application.

EXAMPLE 1

Methods of Making

N-(cyanomethyl)-4-(2-(4-morpholinophenylamino)pyrimidin-4-yl)benzamide (CYT-0387) can be synthesized as described in U.S. Pat. No. 8,486,941 and PCT Application WO 2012/071612.

CYT-0387 dihydrochloride monohydrate Form II from CYT-0387 dihydrochloride anhydrous Form I To a suspension of N-(cyanomethyl)-4-(2-(4-morpholinophenylamino)pyrimidin-4-yl)benzamide (CYT-0387) dihydrochloride anhydrous Form I in methanol was added a molar excess of hydrochloric acid in water. The resulting solids were isolated and washed with methanol and aqueous hydrochloric acid to yield CYT-0387 dihydrochloride monohydrate Form II.

CYT-0387 dihydrochloride monohydrate Form II from CYT-0387 free base

To a suspension of N-(cyanomethyl)-4-(2-(4-morpholinophenylamino)pyrimidin-4-yl)benzamide (CYT-0387) free base in methanol was added a molar excess of concentrated hydrochloric acid. The resulting suspension was optionally seeded with N-(cyanomethyl)-4-(2-(4-morpholinophenylamino)pyrimidin-4-yl)benzamide (CYT-0387) dihydrochloride monohydrate Form II and water was added. The optionally seeded N-(cyanomethyl)-4-(2-(4-morpholinophenylamino)pyrimidin-4-yl)benzamide (CYT-0387) dihydrochloride monohydrate Form II may be prepared as described above. The resulting solids were isolated and washed with methanol and aqueous hydrochloric acid to yield CYT-0387 dihydrochloride monohydrate Form II.

CYT-0387 monohydrochloride anhydrous Form I from CYT-0387 free base

To a suspension of N-(cyanomethyl)-4-(2-(4-morpholinophenylamino)pyrimidin-4-yl)benzamide (CYT-0387) free base in methanol was added 1.0 molar equivalents of concentrated hydrochloric acid. The resulting solids were isolated and washed with methanol to yield CYT-0387 monohydrochloride anhydrous Form I.

CYT-0387 monohydrochloride anhydrous Form III from CYT-0387 monohydrochloride anhydrous Form I A suspension of CYT-0387 monohydrochloride anhydrous Form I is stirred in water/THF (30% water; v/v). The resulting solids were isolated and washed with a water/THF mixture to yield CYT-0387 monohydrochloride anhydrous Form III.

CYT-0387 monohydrochloride anhydrous Form III from CYT-0387 dihydrochloride monohydrate Form II A suspension of CYT-0387 dihydrochloride monohydrate Form II is stirred in methanol/water (30% water; v/v). The resulting solids were isolated and washed with a methanol/water mixture to yield CYT-0387 monohydrochloride anhydrous Form III.

The above forms were characterized by various analytical techniques, including X-ray powder diffraction pattern (XPPD), differential scanning calorimetry (DSC), thermographic analysis (TGA), and dynamic vapor sorption (DVS) using the procedures described below.

X-Ray Powder Diffraction: XRPD analysis was conducted on a diffractometer (PANanalytical XPERT-PRO, PANanalytical B.V., Almelo, Netherlands) using copper radiation (Cu Kα, λ=1.5418 Å). Samples were prepared for analysis by depositing the powdered sample in the center of an aluminum holder equipped with a zero background plate. The generator was operated at a voltage of 45 kV and amperage of 40 mA. Slits used were Soller 0.02 rad., antiscatter 1.0°, and divergence. The sample rotation speed was 2 sec. Scans were performed from 2 to 40° 2θ during 15 min with a step size of 0.0167° 2θ. Data analysis was performed by X'Pert Highscore version 2.2c (PANalytical B.V., Almelo, Netherlands) and X'Pert data viewer version 1.2d (PANalytical B.V., Almelo, Netherlands).

The XRPD pattern for N-(cyanomethyl)-4-(2-(4-morpholinophenylamino)pyrimidin-4-yl)benzamide dihydrochloride monohydrate Form II is represented in FIG. 5.

The XRPD pattern for N-(cyanomethyl)-4-(2-(4-morpholinophenylamino)pyrimidin-4-yl)benzamide monohydrochloride anhydrous Form I is represented in FIG. 6.

The XRPD pattern for N-(cyanomethyl)-4-(2-(4-morpholinophenylamino)pyrimidin-4-yl)benzamide monohydrochloride anhydrous Form III is represented in FIG. 7.

XRPD peaks of the various CYT-0387 forms are found in Table 1 above.

Differential Scanning calorimetry: Thermal properties of N-(cyanomethyl)-4-(2-(4-morpholinophenylamino)pyrimidin-4-yl)benzamide dihydrochloride monohydrate Form II were evaluated using a Differential Scanning calorimetry (DSC) instrument (TA Q1000, TA Instruments, New Castle, Del., USA). Approximately 5 to 10 mg of solid sample was placed in a standard aluminum pan vented with a pinhole for each experiment and heated at a rate of 10° C./min under a 50 mL/min nitrogen purge. Data analysis was conducted using Universal Analysis 2000 Version 4.7A (TA Instruments, New Castle, Del., USA). Heat of fusion analysis was conducted by sigmoidal integration of the endothermic melting peak.

The DSC for N-(cyanomethyl)-4-(2-(4-morpholinophenylamino)pyrimidin-4-yl)benzamide dihydrochloride monohydrate Form II is represented in FIG. 8.

The DSC for N-(cyanomethyl)-4-(2-(4-morpholinophenylamino)pyrimidin-4-yl)benzamide monohydrochloride anhydrous Form I is represented in FIG. 9.

The DSC for N-(cyanomethyl)-4-(2-(4-morpholinophenylamino)pyrimidin-4-yl)benzamide monohydrochloride anhydrous Form III is represented in FIG. 10.

Thermogravimetric Analysis: Thermogravimetric analysis (TGA) of N-(cyanomethyl)-4-(2-(4-morpholinophenylamino)pyrimidin-4-yl)benzamide dihydrochloride monohydrate Form II was performed on a TGA instrument (TA Q500, TA Instruments, New Castle, Del., USA). Approximately 5 to 10 mg of solid sample was placed in an open aluminum pan for each experiment and heated at a rate of 10° C./min under a 60 mL/min nitrogen purge using. Data analysis was conducted using Universal Analysis 2000 Version 4.7A (TA Instruments, New Castle, Del., USA).

The TGA for N-(cyanomethyl)-4-(2-(4-morpholinophenylamino)pyrimidin-4-yl)benzamide dihydrochloride monohydrate Form II is represented in FIG. 11.

The TGA for N-(cyanomethyl)-4-(2-(4-morpholinophenylamino)pyrimidin-4-yl)benzamide monohydrochloride anhydrous Form I is represented in FIG. 12.

The TGA for N-(cyanomethyl)-4-(2-(4-morpholinophenylamino)pyrimidin-4-yl)benzamide monohydrochloride anhydrous Form III is represented in FIG. 13.

Dynamic Vapor Sorption: The hygroscopicity of N-(cyanomethyl)-4-(2-(4-morpholinophenylamino)pyrimidin-4-yl)benzamide dihydrochloride monohydrate Form II was evaluated at room temperature using a dynamic vapor sorption (DVS) instrument (TGA Q5000 TA Instruments, New Castle, Del.). Water adsorption and desorption were studied as a function of relative humidity (RH) over the range of 0 to 90% at room temperature. The humidity in the chamber was increased from the initial level 50% RH) to 60% RH and held until the solid and atmosphere reached equilibration. The equilibrium test was continued until passed or expired after 10 hours. At this point, RH was raised 10% higher and the process was repeated until 90% RH was reached and equilibrated. During this period, the water sorption was monitored. For desorption, the relative humidity was decreased in a similar manner to measure a full sorption/desorption cycle. All experiments were operated in dm/dt mode (mass variation over time) to determine the equilibration endpoint. Approximately 4 mg of solid CYT-0387 was used. Data analysis was conducted using Universal Analysis 2000 Version 4.7A (TA Instruments, New Castle, Del., USA).

The DVS for N-(cyanomethyl)-4-(2-(4-morpholinophenylamino)pyrimidin-4-yl)benzamide dihydrochloride monohydrate Form II is represented in FIG. 14.

The single crystal X-ray crystallography data for N-(cyanomethyl)-4-(2-(4-morpholinophenylamino)pyrimidin-4-yl)benzamide (CYT-0387) dihydrochloride monohydrate Form II and N-(cyanomethyl)-4-(2-(4-morpholinophenylamino)pyrimidin-4-yl)benzamide CYT-0387) monohydrochloride anhydrous Form I is summarized in Table 2 below. Data from further characterization of the crystals are summarized in Table 3 below.

TABLE 2

Single Crystal X-ray Crystallography Data

| Form and Composition | | Unit Cell Dimensions | | | | | |
|---|---|---|---|---|---|---|---|
| | | Distance (Å) | | | Angle (°) | | |
| Form | API:water:solvent | a | b | c | α | β | γ |
| CYT-0387 dihydrochloride monohydrate Form II | 1:1:0 | 10.2837(6) | 10.4981(6) | 11.5143(7) | 83.297(2) | 87.649(2) | 67.445(2) |
| CYT-0387 monohydrochloride anhydrous Form I | 1:0:0 | 9.4255(3) | 11.6729(4) | 19.7561(6) | 85.3940(10) | 88.103(2) | 83.821(2) |

TABLE 3

Crystal Data and Structure Refinement

| Property | CYT-0387 dihydrochloride monohydrate Form II | CYT-0387 monohydrochloride anhydrous Form I |
|---|---|---|
| Empirical formula | $C_{23}H_{26}Cl_2N_6O_3$ | $C_{23}H_{23}ClN_6O_2$ |
| Formula weight | 505.40 | 450.92 |
| Temperature | 100(2) K | 100(2) K |

TABLE 3-continued

| Crystal Data and Structure Refinement | | |
|---|---|---|
| Property | CYT-0387 dihydrochloride monohydrate Form II | CYT-0387 monohydrochloride anhydrous Form I |
| Wavelength | 1.54178 Å | 1.54178 Å |
| Crystal system | Triclinic | Triclinic |
| Space group | P-1 | P-1 |
| Volume | 1140.14(12) $Å^3$ | 2153.36(12) $Å^3$ |
| Z | 2 | 4 |
| Density (calculated) | 1.472 $g/cm^3$ | 1.391 $g/cm^3$ |

100(2) K represents 100 ± 2° K

Microscopic images of the various forms of the invention were acquired using an Olympus polarizing microscope (BX-51, Olympus, Center Valley, Pa., USA). The samples were dispersed in mineral oil and examined under cross-polarized light using a 530 nm wave plate (results not shown).

EXAMPLE 2

Tablets comprising CYT-0387 dihydrochloride monohydrate Form II in amounts equivalent to 100 mg, 150 mg, and 200 mg of CYT-0387 free base can be prepared according to the process described herein. Tablets comprising CYT-0387 dihydrochloride monohydrate Form II in amounts equivalent to 100 mg, 150 mg, 200 mg, 250 mg, and 300 mg of CYT-0387 free base were prepared. The below Table 4, summarizes the formulations of such tablets.

TABLE 4

| Tablet Formulation | | | | | | |
|---|---|---|---|---|---|---|
| | Quantity per Dosage Unit | | | | | |
| Component | Amount (% w/w) | 100 g Strength (mg) | 150 mg Strength (mg) | 200 mg strength (mg) | 250 mg strength (mg) | 300 mg strength (mg) |
| CYT-0387 Dihydrochloride Monohydrate Form II | 40.65 | 121.94 | 182.91 | 243.88 | 304.88 | 365.85 |
| Propyl Gallate | 0.20 | 0.60 | 0.90 | 1.20 | 1.50 | 1.80 |
| Micro-crystalline Cellulose (PH 105) | 34.23 | 102.70 | 154.05 | 205.40 | 256.73 | 308.07 |
| Lactose (Fast Flo 316) | 16.92 | 50.76 | 76.14 | 101.52 | 126.9 | 152.28 |
| Sodium Starch Glycolate | 6.00 | 18.00 | 27.00 | 36.00 | 45.00 | 54.00 |
| Colloidal Silicon Dioxide | 0.50 | 1.50 | 2.25 | 3.00 | 3.75 | 4.50 |
| Magnesium Stearate | 1.50* | 4.50 | 6.750 | 9.00 | 11.25 | 13.50 |
| Core Tablet Total | 100.00 | 300.00 | 450.00 | 600.00 | 750.00 | 900.00 |
| Opadry II Brown 85F165010 | 4.00 | 12.00 | 18.00 | 24.00 | 30.00 | 36.00 |
| Film-Coated Tablet Total | 104.00 | 312.00 | 468.00 | 624.00 | 780.00 | 936.00 |

*0.75% intragranular, 0.75% extragranular Mg stearate

The tablet formulation of Table 4 comprised propyl gallate, which decreased the extent or levels of oxidative degradation of CYT-0387 Form II and resulted in increased stability of CYT-0387 Form II. This was determined from the study that investigated the potential effects of different antioxidants in inhibiting or preventing degradation of CYT-0387 dihydrochloride monohydrate Form II. In the initial study, five antioxidants of three different mechanisms of action were examined: free radical scavenger antioxidants (propyl gallate, butylated hydroxyanisole (BHA), and butylated hydroxytoluene (BHT)), a sacrificial reductant (ascorbic acid), and an oxygen scavenger (sodium metabisulfite).

Aqueous solutions containing 20 μg/mL of CYT-0387 dihydrochlorid monohydrate Form II in 70% (v/v) 50 mM acetate buffer (pH 4.0) and 30% (v/v) methanol were incubated in absence (which was used as control) and presence of 0.1% (w/v) antioxidant at 60° C. for up to 7 days. At Day 0, 5 and 7, the solution was analyzed using a reverse-phase HPLC with a Zorbax SB-C8 column (Phenomenex, Torrance, Calif.). As shown in Table 7, the presence of propyl gallate, BHA, or ascorbic acid, at the level of 0.1% (w/v), inhibited or prevented the degradation of CYT-0387 Form II relative to BHT and sodium metabisulfite at the same level. Less than one percent of CYT-0387 Form II was degraded in the presence of propyl gallate or BHA. While total degradation products could not be determined for 0.1% ascorbic acid due to interference, the main oxidative degradation products were not observed (data not shown).

In additional studies, the effects of the lower concentrations of 0.01% and 0.001% (w/v) of propyl gallate, BHA, and ascorbic acid on the stability of CYT-0387 were examined under the same condition. The results from these studies are summarized in Table 7. The results showed that, at 0.01% (w/v) antioxidant level, increased stability of CYT-0387 Form II was observed in the presence of propyl gallate or ascorbic acid at 60° C. for up to 7 days. Moreover, at 0.001% (w/v) antioxidant level, the presence of propyl gallate decreased or inhibited the degradation of CYT-0387 relative to BHA and ascorbic acid (Table 7). These results indicated that, among the tested antioxidants, propyl gallate was the most effective in inhibiting or preventing the degradation of CYT-0387 dihydrochloride monohydrate Form II.

TABLE 7

| Effects of antioxidants on degradation of CYT-0387 Form II in pH 4 aqueous buffer at 60° C. | | | |
|---|---|---|---|
| Antioxidant | Amount (% w/v) | Time Point (Days) | Total Degradation[a] (%) |
| Control | 0 | 0 | 0.29 |
| | | 5 | 17.24 |
| | | 7 | 21.84 |
| Butylated hydroxytoluene (BHT) | 0.1 | 0 | 0.06 |
| | | 5 | 1.71 |
| | | 7 | 4.35 |
| Sodium Metabisulfite | 0.1 | 0 | 0.33 |
| | | 5 | 43.83 |
| | | 7 | 46.31 |
| Propyl gallate | 0.1 | 0 | 0.29 |
| | | 5 | 0.31 |
| | | 7 | 0.32 |
| | 0.01 | 0 | 0.22 |
| | | 5 | 0.38 |
| | | 7 | 0.72 |
| | 0.001 | 0 | 0.22 |
| | | 5 | 1.98 |
| | | 7 | 4.32 |
| Butylated hydroxyanisole (BHA) | 0.1 | 0 | 0.45 |
| | | 5 | 0.50 |
| | | 7 | 1.24 |

TABLE 7-continued

Effects of antioxidants on degradation of CYT-0387 Form II in pH 4 aqueous buffer at 60° C.

| Antioxidant | Amount (% w/v) | Time Point (Days) | Total Degradation[a] (%) |
|---|---|---|---|
| | 0.01 | 0 | 0.55 |
| | | 5 | 1.75 |
| | | 7 | 3.04 |
| | 0.001 | 0 | 0.30 |
| | | 5 | 7.64 |
| | | 7 | 13.76 |
| Ascorbic Acid | 0.1 | 0 | N/A[b] |
| | | 5 | N/A[b] |
| | | 7 | N/A[b] |
| | 0.01 | 0 | 0.20 |
| | | 5 | 1.58 |
| | | 7 | 1.78 |
| | 0.001 | 0 | 0.51 |
| | | 5 | 17.95 |
| | | 7 | 21.28 |

[a]Include impurity that was present in the formulation
[b]N/A: Not available

Next, the stability of 100 mg tablet formulation comprising CYT-0387 Form II was examined in the presence of 0%, 0.2%, 0.5%, or 1.0% propyl gallate at 25° C./60% RH (relative humidity) or 40° C./75% RH for up to 6 months. The degradation profiles were determined at month 0, 1, 3, and 6. Results of the studies at 40° C./75% RH for up to 6 months were summarized in Table 8. The results showed that, at 40° C./75% RH, CYT-0387 Form II tablet formulation, at 100 mg, having 0.2% propyl gallate exhibited increased stability compared to CYT-0387 Form II tablet formulation, at 100 mg, having 0%, 0.5% or 1.0% propyl gallate. The results of the study at 25° C./60% RH showed that the degradation of CYT-0387 Form II was also reduced by propyl gallate at 0.2%, 0.5%, and 1.0% (data not shown). The observed trend was similar for the degradation profiles at 25° C./60% RH as that observed at 40° C./75% RH, i.e. increased stability of CYT-0387 Form II in the tablet formulation was observed in 0.2% propyl gallate compared to 0%, 0.5%, and 1% propyl gallate (data not shown). Taken together, these results indicate that, among the anti-oxidants and the percentages that were examined in these studies, propyl gallate at 0.2% provided the optional level of stability of CYT-0387 dihydrochloride monohydrate Form II.

TABLE 8

Effects of levels of propyl gallate on degradation of CYT-0387 Form II in the 100 mg tablet formulation.

| Propyl Gallate (%) | Time Point (Months) | Total Degradation (%) |
|---|---|---|
| 0 | 0 | 0.10 |
| | 1 | 0.68 |
| | 3 | 1.01 |
| | 6 | 1.28 |
| 0.2 | 0 | 0.10 |
| | 1 | 0.34 |
| | 3 | 0.67 |
| | 6 | 0.80 |
| 0.5 | 0 | 0.11 |
| | 1 | 0.39 |
| | 3 | 0.67 |
| | 6 | 0.95 |
| 1.0 | 0 | 0.14 |
| | 1 | 0.44 |
| | 3 | 0.87 |
| | 6 | 1.34 |

EXAMPLE 3

Tablets comprising CYT-0387 dihydrochloride monohydrate Form II (doses equivalent to 100, 150, 200, and 300 mg of the free base) and capsules comprising CYT-0387 dihydrochloride anhydrous Form I (dose equivalent to 300 mg of the free base) were evaluated in a Phase 1, single dose study in healthy subjects.

Intensive PK and PD sampling occurred from 0.5 hour up to 36 hours post dose. Safety was monitored throughout the study. A parametric analysis of variance (ANOVA) using a mixed-effects model was used to fit to the natural logarithmic transformation of PK parameters (AUC and $C_{max}$). The 90% confidence intervals were constructed for the ratio of geometric means of CYT-0387 dihydrochloride monohydrate Form II tablets at 100, 150, 200 and 300 mg vs CYT-0387 dihydrochloride anhydrous Form I capsule at 300 mg, using equivalence bounds of 70% to 143% for AUC and $C_{max}$. The pharmacokinetic data is represented in Table 5.

TABLE 5

Pharmacokinetic data of CYT-0387 dihydrochloride monohydrate Form II tablet and CYT-0387 dihydrochloride anhydrous Form I capsule formulations

| CYT-0387 dihydrochloride monohydrate Form II Tablet Dose | Plasma PK Parameters | Tablet: Mean (SD) | CYT-0387 dihydrochloride anhydrous Form I 300 mg capsule Mean (SD) | GMR (%) (90% CI) |
|---|---|---|---|---|
| 100 mg | $AUC_{inf}$ (h · ng/mL) | 1360 (497.9) | 2813 (1984) | 55.8 (42.1, 73.9) |
| | $C_{max}$ (ng/mL) | 166.5 (73.3) | 388.8 (225.0) | 47.3 (35.4, 63.2) |
| 150 mg | $AUC_{inf}$ (h · ng/mL) | 3018 (1532) | 4285 (1923) | 69.9 (59.6, 81.9) |
| | $C_{max}$ (ng/mL) | 354.8 (150.6) | 549.3 (259.9) | 65.6 (55.2, 77.8) |
| 200 mg | $AUC_{inf}$ (h · ng/mL) | 2572 (1671) | 2672 (1993) | 101.9 (87.7, 118.4) |
| | $C_{max}$ (ng/mL) | 323.7 (188.3) | 356.1 (195.6) | 92.0 (79.0, 107.1) |
| 300 mg | $AUC_{inf}$ (h · ng/mL) | 3194 (1445) | 2586 (1481) | 136.2 (107.5, 172.4) |
| | $C_{max}$ (ng/mL) | 415.3 (183.2) | 381.8 (200.8) | 115.7 (87.7, 152.7) |

EXAMPLE 4

CYT-0387 is a selective small molecule inhibitor of Janus kinase 1 and 2 (JAK1/JAK2) currently under investigation to treat myelofibrosis. This study evaluated the mass balance/recovery, metabolite profile, pharmacokinetics, and safety of radiolabeled CYT-0387 in humans.

Six healthy individuals (subjects) received a single oral dose of 200 mg CYT-0387 containing ~100 μCi of [$^{14}$C]-CYT-0387. Blood samples were collected up to 21 days or until plasma radioactivity in 2 consecutive samples was below detection limit or urine and feces sampling was discontinued. Urine/feces samples were collected up to 21 days or until ≥90% administered dose was recovered in feces and urine and radioactivity in 2 consecutive sampling intervals were ≤1% administered dose. Plasma concentrations of CYT-0387 and metabolites were measured using LC-MS/MS and total radioactivity assessed by liquid scintillation counting. Metabolite profiling was performed in select urine, feces, and plasma samples. Safety assessments were performed throughout the study.

Results: CYT-0387 was well tolerated. No Grade 3 or 4 AEs, SAES, or AEs leading to study discontinuation were reported. The most frequently reported AEs were dizziness, headache, and nausea. Maximum concentration of drug-derived radioactivity in plasma was observed at 2.5 hours postdose. Mean blood-to-plasma concentration ratios ranged from 0.7 to 0.9 through 24 hours postdose, indicating low association of radioactivity with blood cells. Overall recovery of radioactivity was 96.7% (feces: 69.3%; urine: 27.5%). The circulating radioactivity consisted mainly of metabolite M21 (64.2%), CYT-0387 (17.3%), and metabolites (M8: 5.8%; metabolite M19: 5.2%; M5: 2.7%; M28: 2.5%; and M20: 2.3%). The major component excreted in feces was M14 (21.4% of the dose), along with CYT-0387 (12.6% of the dose) and other metabolites (M21: 12.7% of the dose; co-eluted M19/M33: 7.1% of the dose). The remaining identified 10 metabolites in feces each accounted for less than 5% of the dose. In urine, metabolite M21 was the main species (11.5% of the dose), with low levels of minor metabolites observed.

After oral administration in healthy subjects, [$^{14}$C]-CYT-0387 was primarily eliminated in the feces, as a combination of metabolites and unchanged parent drug.

EXAMPLE 5

CYT-0387 is a selective small molecule inhibitor of Janus kinase 1 and 2 (JAK1/JAK2), and is currently under investigation to treat myelofibrosis. In a Phase 1/2 study in myelofibrosis patients, 300 mg CYT-0387 capsule once daily was selected as Phase 3 dose based on a favorable benefit:risk profile. An immediate release tablet formulation (CYT-0387 tablet) was developed for further clinical evaluation. The relative bioavailability of CYT-0387 tablet vs capsule was evaluated in this study to identify Phase 3 dose of CYT-0387 tablet. CYT-0387 tablet (100 to 300 mg) vs capsule (300 mg) pharmacokinetics (PK) after a single dose was evaluated in healthy subjects. CYT-0387 tablet PK at supratherapeutic doses (400 and 800 mg), under fed and fasted conditions, and with an acid reducing agent (i.e., omeprazole) was also evaluated. Intensive PK sampling occurred up to 36 hours postdose. Safety was monitored throughout the study. A parametric analysis of variance (ANOVA) using a mixed-effects model was used to fit to the natural logarithmic transformation of PK parameters (AUC and $C_{max}$). The 90% confidence intervals were constructed for the ratio of geometric means of CYT-0387 tablet PK at 100, 150, 200 and 300 mg vs CYT-0387 capsule 300 mg, using equivalence bounds of 70% to 143% for AUC and $C_{max}$. A similar approach was used to assess the effect of food and omeprazole.

CYT-0387 tablet at 200 mg provided plasma exposures equivalent to CYT-0387 capsule at 300 mg (Table 6). CYT-0387 plasma exposures increased less-than-dose-proportionally from 100 to 800 mg. Intake of light and high-fat meal modestly increased $C_{max}$ (38% and 28% increase for light- and high-fat meals, respectively) and $AUC_{inf}$ (16% and 28% increase for light- and high-fat meals, respectively) for CYT-0387 tablet. Omeprazole reduced the exposure of CYT-0387 tablet by 36% for $C_{max}$ and 33% for $AUC_{inf}$. These differences were not considered clinically relevant.

CYT-0387 tablet at 200 mg provides comparable exposure to CYT-0387 capsule at 300 mg. CYT-0387 tablet plasma exposures increased in a less-than-dose-proportional manner. No clinically relevant effects of food or acid reducing agents were observed on CYT-0387 tablet PK.

TABLE 6

Relative bioavailability of CYT-0387 phase 3 tablet vs capsule following single dose CYT-0387 administration

| PK Parameters | 200 mg Tablet: Mean (% CV) | 300 mg Capsule: Mean (% CV) | GMR [%] (90% CI) |
|---|---|---|---|
| $C_{max}$ (ng/mL) | 323.7 (58.2) | 356.1 (54.9) | 91.99 (78.98, 107.15) |
| $AUC_{inf}$ (h · ng/mL) | 2549.7 (66.1) | 2665.5 (74.9) | 101.69 (87.45, 118.26) |
| $AUC_{last}$ (h · ng/mL) | 2324.5 (65.3) | 2443.9 (71.3) | 100.35 (86.73, 116.10) |

% CV = % coefficient of variation;

CI = confidence interval; data rounded as applicable and shown as three significant figures

EXAMPLE 6

This example described the preparation of M14 (Compound 3), M8 (Compound 4), M20 (Compound 12), M21 (Compound 13), Compound 8 and Compound 10.

To a flask was charged 4-(2-chloropyrimidin-4-yl)benzoic acid (3.0 g, 12.8 mmol), 4-morpholonoaniline (2.7 g, 14.0 mmol, 1.1 equiv), and NMP (30 mL) The resulting solution was stirred at 120° C. Upon completion, the reaction was cooled and added with 30 mL of aqueous $NaHCO_3$. The resulting slurry was filtered, rinsed with water, and dried under vacuum at 45° C. to provide 4-(2-((4-(3-oxomorpholino)phenyl)amino)pyrimidin-4-yl)benzoic acid (Compound 3) having the below structure:

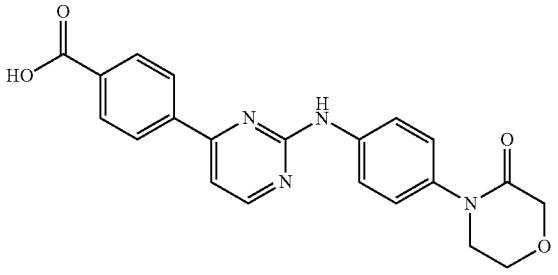

$^1$H NMR (400 MHz, DMSO-$d_6$): δ=13.21 (s, 1H), 9.85 (s, 1H), 8.62 (d, J=5.2 Hz, 1H), 8.28 (d, J=8.2 Hz, 2H), 8.10 (d, J=8.2 Hz, 2H), 7.85 (d, J=8.4 Hz, 2H), 7.49 (d, J=5.2 Hz, 1H), 7.33 (d, J=9.0 Hz, 2H), 4.19 (s, 2H), 3.98 (m, 2H), 3.71 (m, 2H)

To a flask was charged Compound 3 (1.0 g, 2.43 mmol), TBTU (1.0 g, 3.15 mmol, 1.3 equiv), glycinamide hydrochloride (0.32 g, 1.2 equiv.), DMSO (9 mL) and i-$Pr_2$NEt (0.65 g, 2.92 mmol, 1.2 equiv.). Upon reaction completion, water (7.7 mL) was added and the resulting slurry was filtered and rinsed with DMSO/water (2:1) and water. The isolated solids were reslurried in 10 mL of MeOH, filtered, washed with MeOH, and dried in a vacuum oven at 45° C. to provide N-(2-amino-2-oxoethyl)-4-(2-((4-(3-oxomorpholino)phenyl)amino)pyrimidin-4-yl)benzamide (Compound 4) having the below structure:

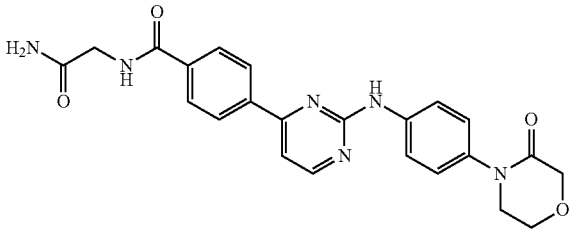

$^1$H NMR (400 MHz, DMSO-$d_6$): δ=9.83 (s, 1H), 8.81 (t, J=6.0 Hz, 1H), 8.60 (d, J=2.9 Hz, 1H), 8.27 (d, J=8.5 Hz, 2H), 8.05 (d, J=8.4 Hz, 2H), 7.85 (d, J=6.9 Hz, 2H), 7.51 (d, J=4.8 Hz, 1H), 7.41 (bs, 1H), 7.32 (d, J=8.9 Hz, 2H), 7.06 (bs, 1H), 4.19 (s, 2H), 3.98 (m, 2H), 3.85 (d, J=5.8 Hz, 2H), 3.72 (m, 2H); HRMS (ESI+): calcd. for $C_{23}H_{23}N_6O_4$ $[M+H]^+$: 447.18 found: 447.19.

A suspension of {4-[(cyanomethyl)carbamoyl]phenyl}boronic acid (4.2 g, 20.6 mmol), 2,4-dichloropyrimidine (4.3 g, 28.8 mmol), potassium carbonate (2.8 kg, 20.6 mmol) and [1,1'-bis(diphenylphosphino)ferrocene]dichloropalladium(II), complex with dichloromethane (1:1) (84 mg, 0.10 mmol) in acetonitrile (21 mL) and water (11 mL) was sparged with $N_2$ for 30 minutes. The mixture was heated to 75° C. until the reaction was complete. The mixture was cooled to 60° C. and the layers were separated. An aqueous N-acetyl cysteine solution (6 mL) was added followed by the addition of water (15 mL). The mixture was cooled to 20° C. The solids were filtered, washed with $H_2O/CH_3CN$ (3:1), and dried at 50° C. to provide 4-(2-chloropyrimidin-4-yl)-N-(cyanomethyl)benzamide having the below structure:

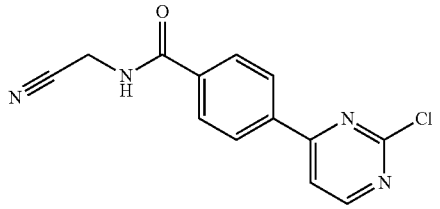

$^1$H NMR (300 MHz, DMSO-$d_6$): δ 4.36 (d, J=5.5 Hz, 2H), 8.05 (m, J=8.5 Hz, 2H), 8.24 (d, J=5.3 Hz, 1H), 8.32 (m, J=8.5 Hz, 2H), 8.89 (d, J=5.2 Hz, 1H), 9.39 (t, J=5.5 Hz, 1H). HRMS (ESI+): calcd. for $C_{13}H_{10}ClN_4O$ [M+1]: 273.15 found 273.25.

To a flask was charged 4-(2-chloropyrimidin-4-yl)-N(cyanomethyl)benzamide (6.7 g, 24.6 mmol), 2-((4-aminophenyl)amino)ethanol (7.5 g, 49.3 mmol, 2.0 equiv), i-$Pr_2$NEt (4.8 g, 36.9 mmol, 1.5 equiv.), and DMSO (20 mL). The resulting solution was stirred at 100° C. Upon reaction completion, the solution was cooled to 20° C. then added onto 135 mL of water. The resulting slurry was filtered and rinsed with 70 mL of water. The solids were reslurried in i-PrOH (70 mL). The resulting slurry was filtered and rinsed with i-PrOH. The solids were dried under vacuum and dissolved in 30 mL of THF and heated to 50° C. Water (85 mL) was slowly charged and the slurry was cooled to 20° C. The resulting solids were isolated by filtration, rinsed with THF/water (1:3) and water, and dried at 40° C. to provide N-(cyanomethyl)-4-(2((4-((2-hydroxyethyl)amino)phenyl)amino)pyrimidin-4-yl)benzamide (Compound 8) having the below structure:

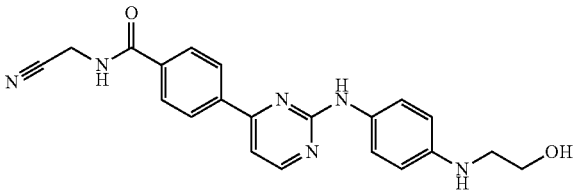

$^1$H NMR (DMSO-$d_6$): 9.33 (t, J=5.5 Hz, 1H), 9.24 (s, 1H), 8.48 (d, J=5.1 Hz, 1H), 8.24 (d, J=8.4 Hz, 2H), 8.01 (d, J=8.5 Hz, 2H), 7.46 (d, J=8.8 Hz, 2H), 7.33 (d, J=5.2 Hz, 1H), 6.58 (d, J=8.9 Hz, 2H), 5.20 (t, J=5.8 Hz, 1H), 4.66 (t, J=5.4 Hz, 1H), 4.35 (d, J=5.4 Hz, 2H), 3.57 (q, J=5.8 Hz, 2H), 3.08 (q, J=5.8 Hz, 2H); HRMS (ESI+): calcd. for $C_{21}H_{21}N_6O_2$ [M+1]: 389.17 found 389.27.

To a flask was charged 4-(2-chloropyrimidin-4-yl)-N-(cyanomethyl)benzamide (4.0 g, 14.7 mmol), phenylenediamine (3.2 g, 29.3 mmol, 2.0 equiv), i-$Pr_2$NEt (2.9 g, 22.1 mmol, 1.5 equiv.), and DMSO (12 mL). The resulting solution was stirred at 60° C. Upon reaction completion, the mixture was cooled to 20° C. then added onto 50 mL of water. The resulting slurry was filtered and rinsed with water followed by i-PrOH. The solids were reslurried in i-PrOH (50 mL), filtered, rinsed with i-PrOH, and dried at 40° C. to afford 4-(2-((4-aminophenyl)amino)pyrimidin-4-yl)-N-(cyanomethyl)benzamide (Compound 10) having the below structure:

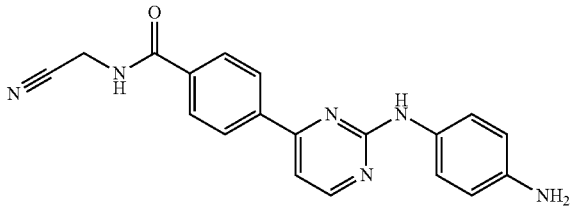

$^1$H NMR (400 MHz, DMSO-$d_6$): 6=9.33 (t, J=5.6 Hz, 1H), 9.21 (s, 1H), 8.47 (d, J=5.2 Hz, 1H), 8.24 (d, J=8.5 Hz, 2H), 8.01 (d, J=8.2 Hz, 2H), 7.39 (d, J=8.4 Hz, 2H), 7.33 (d, J=5.1 Hz, 1H), 6.56 (d, J=8.4 Hz, 2H), 4.78 (bs, 2H), 4.36 (d, J=6.4 Hz, 2H); HRMS (ESI+): calcd. for $C_{19}H_{17}N_6O$ [M+H]: 345.15 found 345.28.

To a flask was charged 4-(2-chloropyrimidin-4-yl)-N-(cyanomethyl)benzamide (4.0 g, 14.7 mmol), 4'-aminoacetanilide (2.6 g, 17.6 mmol, 1.2 equiv), i-$Pr_2$NEt (2.9 g, 22.1 mmol, 1.5 equiv.), and DMSO (12 mL). The resulting solution was stirred at 120° C. Upon reaction completion, the mixture was cooled to 20° C. and MeOH (30 mL) was slowly added. The resulting slurry was filtered and rinsed with MeOH. The solids were reslurried in 40 mL of MeOH, filtered, rinsed with MeOH, and dried at 40° C. to afford 4-(2-((4-acetamidophenyl)amino)pyrimidin-4-yl)-N-(cyanomethyl)benzamide (Compound 12) having the below structure:

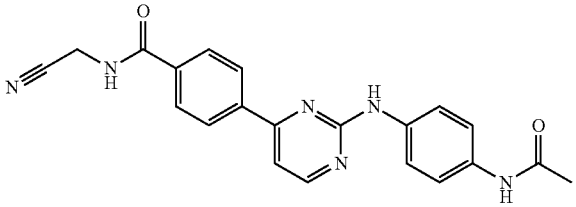

$^1$H NMR (DMSO-$d_6$): 9.82 (s, 1H), 9.64 (s, 1H), 9.33 (t, J=5.5 Hz, 1H), 8.57 (d, J=5.1 Hz, 1H), 8.28 (d, J=8.1 Hz, 2H), (8.04, J=8.5 Hz, 2H), 7.72 (d, J=8.9 Hz, 2H), 7.52 (d, J=8.9 Hz, 2H), 7.45 (d, J=5.0 Hz, 1H), 4.36 (d, J=5.3 Hz, 2H), 2.03 (s, 3H); HRMS (ESI+): calcd. for $C_{21}H_{19}N_6O_2$ [M+1]: 387.16 found 387.28.

A mixture of 4-(2-chloropyrimidin-4-yl)-N-(cyanomethyl)benzamide (2.0 g, 7.2 mmol), 4-(4-aminophenyl)morpholin-3-one (1.4 g, 7.2 mmol) and zinc dichloride (98 mg, 0.72 mmol) in N-methylpyrrolidinone (10 mL) was sparged with $N_2$ for 10 minutes, then heated to 90° C. until the reaction was deemed complete. The mixture was cooled to 50° C. and water (15 mL) was then slowly added to the reaction mixture. The resulting slurry was cooled to 20° C. and the solids were filtered, rinsed with water and dried. The solids were dissolved in 15 mL of DMSO and heated to 50° C. Methanol (25 mL) was added to the mixture and then cooled to 20° C. The resulting solids were filtered, rinsed with MeOH, and dried at 60° C. under vacuum to afford N-(cyanomethyl)-4-(2-{[4-(3-oxomorpholin-4-yl)phenyl]amino}lpyrimidin-4-yl)benzamide (Compound 13) having the below structure:

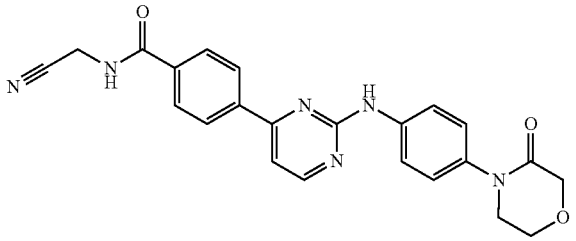

$^1$H NMR (300 MHz, DMSO-$d_6$): δ 9.83 (s, 1H), 9.34 (t, J=5.5 Hz, 1H), 8.62 (d, J=5.2 Hz, 1H), 8.30 (m, J=8.6 Hz, 2H), 8.04 (m, J=8.6 Hz, 2H), 7.85 (m, J=8.9 Hz, 2H), 7.51 (d, J=5.2 Hz, 1H), 7.33 (m, J=8.9 Hz, 2H), 4.36 (d, J=5.4 Hz, 2H), 4.20 (s, 2H), 3.98 (dd, J=5.9, 4.19 Hz, 2H), 3.62-3.79 (m, 2H). HRMS (ESI+): calcd. for $C_{23}H_{21}N_6O_3$[M+1]: 429.17 found 429.0.

EXAMPLE 7

This study characterized the effect of CYT-0387 on hepcidin production in HepG2 cells, a hepatocellular carcinoma cell line. Bone morphogenic proteins (BMPs) is shown to be involved in the transcriptional induction of hepcidin in hepatocytes by facilitating the association of constitutively active Type-II BMP receptor kinases (BMPR-kinase) with Type-I BMPR-kinase (Andriopoulos, et al. Nat Genet, 2009. 41(4): p482-7; Zhao, et al., J Clin Invest, 2013. 123(6): p2337-43). This results in phosphorylation and activation of Type-I BMPR-kinases and subsequent downstream activation of effector SMAD proteins (SMAD1/5/8) followed by nuclear translocation in association with SMAD4 (Wrana, Cold Spring Harb Perspect Biol, 2013. 5:a011197).

HepG2 cells were preincubated for 2 hours with CYT-0387 (ranging from 0 μM to 10 μM) in the presence of 1% FBS then stimulated for 6 hours with 10 ng/mL of BMP6. Total RNA was isolated from the cells and analyzed for the levels of hepcidin by qRT-PCR. GUSB (glucuronidase, beta) was used as a house keeping control to normalize the levels measured by qRT-PCR. The percentage of hepcidin fold-change induction was calculated (100% is equal to hepcidin induction in vehicle treated cells) and summarized in Table 9. The results showed that CYT-0387 resulted in a dose-dependent inhibition of BMP6-mediated hepcidin induction.

HepG2 cells were preincubated for 2 hours with increasing concentrations of CYT-0387 (0.02 to 10 μM CYT387) in the presence of 1% FBS and then stimulated for 30 minutes with 10 ng/mL of BMP6. Protein was extracted from the lysed cells and analyzed using immunoblot analysis with the antibodies specific for phospho-SMAD1 (Ser463/465), phospho-SMAD5 (Ser463/465) and phospho-SMAD8 (Ser465/467) and β-actin. Raw phospho-SMAD1/5/8 levels were quantified using densitometry software (Image Studio) and normalized to β-actin levels. The percentage of phospho-SMAD1/5/8 levels was calculated (100% is equal to phospho-SMAD1/5/8 levels in vehicle treated cells stimulated with 10 ng/mL of BMP6) and summarized in Table 9. The results showed that CYT-0387 resulted in a dosedependent inhibition of BMP6-mediated phospho-SMAD1/5/8 levels.

TABLE 9

The normalized percentage of hepcidin fold-change induction and phospho-SMAD1/5/8 levels in HepG2 cells stimulated with BMP6 in the presence of CYT-0387.

| CYT-0387 (μM) | hepcidin fold-change induction[a] | SD[b] | phospho-SMAD1/5/8 levels[c] | SD[b] |
|---|---|---|---|---|
| 0 | 100 | 0 | 100 | 0 |
| 0.020 | 115 | 40 | 83 | 28 |
| 0.039 | 91 | 28 | 80 | 11 |
| 0.078 | 74 | 28 | 91 | 14 |
| 0.156 | 86 | 21 | 96 | 10 |
| 0.313 | 89 | 43 | 88 | 18 |
| 0.625 | 45 | 24 | 91 | 16 |
| 1.25 | 28 | 21 | 65 | 14 |
| 2.5 | 6 | 13 | 52 | 15 |
| 5.0 | −4 | 6 | 40 | 9 |
| 10.0 | −3 | 4 | 31 | 11 |

[a]average induction for n = 2.
[b]SD: standard deviation.
[c]average induction for n = 6.

In addition, biochemical binding assays (DiscoveRx) and in vitro enzyme inhibition assays (LanthaScreen, Life Technologies) were conducted to determine the binding affinity and inhibition activities of CYT-0387 to Type-I BMPR-kinases (ALK2, ALK3, and ALK6) were conducted. Transforming growth factor beta receptor 1 (TGFBR1, ALK5) was used as a control to determine the selectivity to Type-I BMPR-kinases. The results were summarized in Table 10 and showed that CYT-0387 had higher affinity and inhibitory activities to ALK2 and ALK6 compared to ALK3.

TABLE 10

Biochemical Kd and $IC_{50}$ values of CYT-0387 to BMPR-kinases.

| | | $IC_{50}$ (nM) | |
|---|---|---|---|
| CYT-0387 | Kd (nM) | AVG[a] | SD[b] |
| ALK2 (Acvr1) | 25 | 8 | 2 |
| ALK3 (BMPR1a) | 1000 | 405 | 131 |

TABLE 10-continued

Biochemical Kd and $IC_{50}$ values of CYT-0387 to BMPR-kinases.

| CYT-0387 | Kd (nM) | $IC_{50}$ (nM) AVG[a] | SD[b] |
|---|---|---|---|
| ALK6 (BMPR1B) | 19 | 107 | 8 |
| TGFBR1 | 670 | 205 | 37 |

[a]AVG: average value for n = 3.
[b]SD: standard deviation.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed:

[1. A compound selected from the group consisting of:

N-(cyanomethyl)-4-(2-(4-morpholinoohenylamino)pyrimidin-4-yl)benzamide dihydrochloride monohydrate Form II;

N-(cyanomethyl)-4-(2-(4-morpholinophenylamino)pyrirnidin-4-yl)benzarnide monohydrochloride anhydrous Form I; and N-(cyanomethyl)-4-(2-(4-morpholinophenylamino)pyrimidin-4-yl)benzamide monohydrochloride anhydrous Form III.]

[2. The compound of claim 1 in a crystalline form.]

[3. The crystalline form of claim 2, wherein the crystalline form is N-(cyanomethyl)-4-(2-(4-morpholinophenylarnino) pyrimidin-4-yl)benzamide dihydrochloride monohydrate Form II.]

[4. The crystalline form of claim 3, wherein the crystals have unit cell parameters at T=100° K of: a=10.2837(6) Å, b=10.4981(6) Å, c=11.5143 (7) Å, α=83.297(2)° ,β=87.649 (2)° , y=67.445(2)° , and a triclinic P-1 space group.]

[5. The crystalline form of claim 3, characterized by an x-ray powder diffraction (XRPD) pattern substantially as set forth in FIG. 5.]

[6. The crystalline form of claim 3, characterized by an x-ray powder diffraction (XRPD) pattern having peaks at about 7.7° , 19.3° , 24.0° , 25.7° , and 29.6°2–θ±0.2° 2–θ.]

[7. The crystalline form of claim 3, characterized by differential scanning calorimetry (DSC) pattern substantially as set forth in FIG. 8.]

[8. The crystalline form of claim 3, characterized by a dynamic vapor sorption (DVS) pattern substantially as set forth in FIG. 14.]

[9. The crystalline form of claim 2, wherein the crystalline form is Crystalline N-(cyanomethyl)-4-(2-(4-morpholinophenylamino)pyrimidin-4-yl)benzamide monohydrochloride anhydrous Form I.]

[10. The crystalline form of claim 9, characterized by an x-ray powder diffraction (XRPD) pattern substantially as set forth in FIG. 6.]

[11. The crystalline form of claim 9, characterized by an X-ray powder diffraction ("XRPD") pattern having peaks at about 13.5° , 20.9° , 26.1° , 26.6° , and 28.3° 2–θ±0.2° 2–θ.]

[12. The crystalline form of claim 9, characterized by a differential scanning calorimetry (DSC) pattern substantially as set forth in FIG. 9.]

[13. The crystalline form of claim 2, wherein the crystalline form is crystalline N-(cyanomethyl)-4-(2-(4-morpholinophenylamino)pyrirnidin-4-yl)benzamide monohydrochloride anhydrous Form III.]

[14. The crystalline form of claim 13, characterized by an x-ray powder diffraction (XRPD) pattern substantially as set forth in FIG. 7.]

[15. The crystalline form of claim 13, characterized by an X-ray powder diffraction (XRPD) pattern having peaks at about 12.7° , 14.6° , 17,8° , 19.7° , and 23.3° 2–θ±0.2° 2–θ.]

[16. The crystalline form of claim 13, characterized by a differential scanning calorimetry (DSC) pattern substantially as set forth in FIG. 10.]

[17. A pharmaceutical composition comprising a compound of claim 1, wherein the pharmaceutical composition is in a solid form.]

[18. The pharmaceutical composition of claim 17, wherein the compound of claim 1 is N-(cyanomethyl)-4-(2-(4-morpholinophenylamino)pyrimidin-4-yl)benzamide dihydrochloride monohydrate Form II.]

[19. The pharmaceutical composition of claim 17 wherein N-(cyanornethyl)-4-(2-(4-morpholinophenylamino)pyrimidin-4-yl)benzamide dihydrochloride monohydrate Form II is present at an amount equivalent to 50 mg, 100 mg, 150 mg, or 200 mg of free base N-(cyanomethyl)-4-(2-(4-morpholinaphenybmino)pyrimidin-4-yl)benzamide.]

[20. The pharmaceutical composition of claim 17 in the form of a tablet.]

[21. The pharmaceutical composition of claim 17, wherein after a single oral administration said composition provides:

a $C_{max}$ in the range of 260 to 405 ng/mL of N-(cyanomethyl)-4-(2-(4-morpholinophenylamino)pyrimidin-4yl) benzamide, an $AUC_{inf}$ in the range of 2,057 to 3,214 ng·hr/mL of N-(cyanomethyl)-4-(2-(4-morpholinophenylamino)pyrimidin-4-yl)benzamide, or both a $C_{max}$ in the range of 260 to 405 ng/ml of N-(cyanomethyl)-4-(2-(4-morpholinophenylamino)pyrimidin-4-yl)benzamide and an $AUC_{inf}$ in the range of 2,057 to 3,214 ng·hr/mL of N-(cyanomethyl)-4-(2-(4-morpholinophenylamino)pyrimidin-4-yl)benzamide.]

[22. The pharmaceutical composition of claim 21, wherein after a single oral administration said composition provides a pharmacokinetic profile substantially similar to that of a dosage form comprising N-(cyanomethyl)-4-(2-(4-morpholinophenylamino)pyrimidin-4-yl)benzamide dihydrochloride anhydrous Form I in an amount equivalent to 300 mg of free base N-(cyanomethyl)-4-(2-(4-morpholinophenylamino)pyrimidin-4-yl)benzamide.]

[23. A method for the treatment of a disease associated with Janus Kinase (JAK) which comprises administering to a subject in need an effective amount of the pharmaceutical composition of claim 18, wherein the disease is a myeloproliferative disease selected from the group consisting of thrombocythemia, idiopathic myelofibrosis, systemic mastocystosis (SM), myelodispiastic syndrome (MDS) and systemic mast cell disease (SMCD).]

24. A pharmaceutical composition comprising a compound having the formula

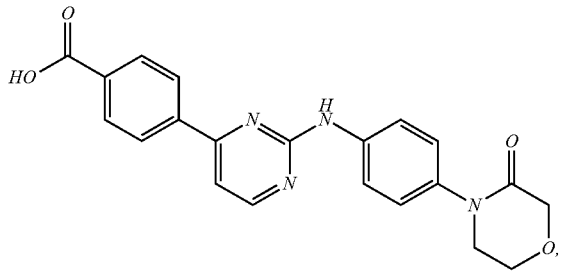

or a pharmaceutically acceptable salt thereof, and a pharmaceutically acceptable excipient or diluent;

wherein one or more hydrogen atoms attached to carbon atoms of the compound are replaced by a deuterium atom.

25. A pharmaceutical composition comprising a compound having the formula

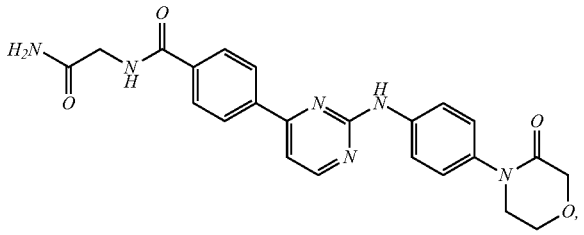

or a pharmaceutically acceptable salt thereof, and a pharmaceutically acceptable excipient or diluent;

wherein one or more hydrogen atoms attached to carbon atoms of the compound are replaced by deuterium atoms.

26. A pharmaceutical composition comprising a compound having the formula

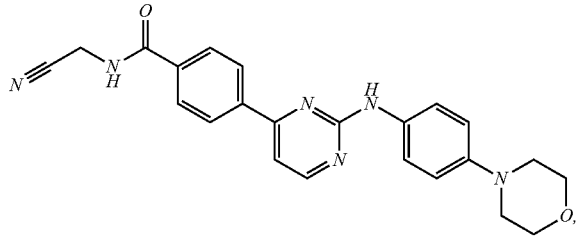

or a pharmaceutically acceptable salt thereof, and a pharmaceutically acceptable excipient or diluent;

wherein one or more hydrogen atoms attached to carbon atoms of the compound are replaced by deuterium atoms.

27. A compound selected from the group consisting of:

N-(cyanomethyl)-4-(2-(4-morpholinophenylamino)pyrimidin-4-yl)benzamide dihydrochloride monohydrate Form II;

N-(cyanomethyl)-4-(2-(4-morpholinophenylamino)pyrimidin-4-yl)benzamide monohydrochloride anhydrous Form I; and N-(cyanomethyl)-4-(2-(4-morpholinophenylamino)pyrimidin-4-yl)benzamide monohydrochloride anhydrous Form III;

wherein one or more hydrogen atoms attached to carbon atoms of the compound are replaced by deuterium atoms.

28. The compound of claim 27 in a crystalline form.

29. The crystalline form of claim 28, wherein the crystalline form is N-(cyanomethyl)-4-(2-(4-morpholinophenylamino)pyrimidin-4-yl)benzamide dihydrochloride monohydrate Form II.

30. The crystalline form of claim 28, wherein the crystalline form is N-(cyanomethyl)-4-(2-(4-morpholinophenylamino)pyrimidin-4-yl)benzamide dihydrochloride monohydrate Form II and the crystals have unit cell parameters at T=100° K of: a =10.2837(6) Å, b=10.4981(6) Å, c=11.5143(7) Å, α=83.297(2)°, β=87.649(2)°, y=67.445 (2)°, and a triclinic P-1 space group.

31. The crystalline form of claim 28, wherein the crystalline form is N-(cyanomethyl)-4-(2-(4-morpholinophenylamino)pyrimidin-4-yl)benzamide dihydrochloride monohydrate Form II and is characterized by an X-ray powder diffraction (XRPD) pattern substantially as set forth in FIG. 5.

32. The crystalline form of claim 28, wherein the crystalline form is N-(cyanomethyl)-4-(2-(4-morpholinophenylamino)pyrimidin-4-yl)benzamide dihydrochloride monohydrate Form II and is characterized by an x-ray powder diffraction (XRPD) pattern having peaks at about 7.7°, 19.3°, 24.0°, 25.7°, and 29.6° 2−θ±0.2° −θ.

33. The crystalline form of claim 28, wherein the crystalline form is N-(cyanomethyl)-4-(2-(4-morpholinophenylamino)pyrimidin-4-yl)benzamide dihydrochloride monohydrate Form II and is characterized by a differential scanning calorimetry (DSC) pattern substantially as set forth in FIG. 8.

34. The crystalline form of claim 28, wherein the crystalline form is N-cyanomethyl)-4-(2-(4-morpholinophenylamino)pyrimidin-4-yl)benzamide dihydrochloride monohydrate Form II and is characterized by a dynamic vapor sorption (DVS) pattern substantially as set forth in FIG. 14.

35. The crystalline form of claim 28, wherein the crystalline form is N-(cyanomethyl)-4-(2-(4-morpholinophenylamino)pyrimidin-4-yl)benzamide monohydrochloride anhydrous Form I.

36. The crystalline form of claim 28, wherein the crystalline form is N-(cyanomethyl)-4-(2-(4-morpholinophenylamino)pyrimidin-4-yl)benzamide monohydrochloride anhydrous Form I and is characterized by an x-ray powder diffraction (XRPD) pattern substantially as set forth in FIG. 6.

37. The crystalline form of claim 28, wherein the crystalline form is N-(cyanomethyl)-4-(2-(4-morpholinophenylamino)pyrimidin-4-yl)benzamide monohydrochloride anhydrous Form I and is characterized by an X-ray powder diffraction (XRPD) pattern having peaks at about 13.5°, 20.9°, 26.1°, 26.6°, and 28.3° 2−θ±0.2° 2−θ.

38. The crystalline form of claim 28, wherein the crystalline form is N-(cyanomethyl)-4-(2-(4-morpholinophenylamino)pyrimidin-4-yl)benzamide monohydrochloride anhydrous Form I and is characterized by a differential scanning calorimetry (DSC) pattern substantially as set forth in FIG. 9.

39. The crystalline form of claim 28, wherein the crystalline form is N-(cyanomethyl)-4-(2-(4-morpholinophenylamino)pyrimidin-4-yl)benzamide monohydrochloride anhydrous Form III.

40. The crystalline form of claim 28, wherein the crystalline form is N-(cyanomethyl)-4-(2-(4-morpholinophenylamino)pyrimidin-4-yl)benzamide monohydrochloride anhydrous Form III and is characterized by an x-ray powder diffraction (XRPD) pattern substantially as set forth in FIG. 7.

41. The crystalline form of claim 28, wherein the crystalline form is N-(cyanomethyl)-4-(2-(4-morpholinophenylamino)pyrimidin-4-yl)benzamide monohydrochloride anhydrous Form III and is characterized by an X-ray powder diffraction (XRPD) pattern having peaks at about 12.7°, 14.6°, 17.8°, 19.7°, and 23.3° 2−θ±0.2° 2−θ.

42. The crystalline form of claim 28, wherein the crystalline form is N-(cyanomethyl)-4-(2-(4-morpholinophenylamino)pyrimidin-4-yl)benzamide monohydrochloride anhydrous Form III and is characterized by a differential scanning calorimetry (DSC) pattern substantially as set forth in FIG. 10.

43. A pharmaceutical composition comprising a compound of claim 27, wherein the pharmaceutical composition is in a solid form.

44. The pharmaceutical composition of claim 43, wherein the compound is N-(cyanomethyl)-4-(2-(4-morpholinophenylamino)pyrimidin-4-yl)benzamide dihydrochloride monohydrate Form II.

45. The pharmaceutical composition of claim 43, wherein N-(cyanomethyl)-4-(2-(4-morpholinophenylamino)pyrimidin-4-yl)benzamide dihydrochloride monohydrate Form II is present in an amount equivalent to 50 mg, 100 mg, 150 mg, or 200 mg of free base N-(cyanomethyl)-4-(2-(4-morpholinophenylamino)pyrimidin-4-yl)benzamide.

46. The pharmaceutical composition of claim 43, wherein the compound is N-(cyanomethyl)-4-(2-(4-morpholinophenylamino)pyrimidin-4-yl)benzamide monohydrochloride anhydrous Form I.

47. The pharmaceutical composition of claim 43, wherein N-(cyanomethyl)-4-(2-(4-morpholinophenylamino)pyrimidin-4-yl)benzamide monohydrochloride anhydrous Form I is present in an amount equivalent to 100 mg, 150 mg, or 200 mg of free base N-(cyanomethyl)-4-(2-(4-morpholinophenylamino)pyrimidin-4-yl)benzamide.

48. The pharmaceutical composition of claim 43, wherein the compound is N-(cyanomethyl)-4-(2-(4-morpholinophenylamino)pyrimidin-4-yl)benzamide monohydrochloride anhydrous Form III.

49. The pharmaceutical composition of claim 43, wherein N-(cyanomethyl)-4-(2-(4-morpholinophenylamino)pyrimidin-4-yl)benzamide monohydrochloride anhydrous Form III is present in an amount equivalent to 100 mg, 150 mg, or 200 mg of free base N-(cyanomethyl)-4-(2-(4-morpholinophenylamino)pyrimidin-4-yl)benzamide.

50. The pharmaceutical composition of claim 43 in the form of a tablet.

51. The pharmaceutical composition of claim 43, wherein after a single oral administration said composition provides:

a $C_{max}$ in the range of 260 to 405 ng/mL of N-(cyanomethyl)-4-(2-(4-morpholinophenylamino)pyrimidin-4-yl)benzamide, an $AUC_{inf}$ in the range of 2,057 to 3,214 ng·hr/mL of N-(cyanomethyl)-4-(2-(4-morpholinophenylamino)pyrimidin-4-yl)benzamide, or both a $C_{max}$ in the range of 260 to 405 ng/ml of N-(cyanomethyl)-4-(2-(4-morpholinophenylamino)pyrimidin-4-yl)benzamide and an $AUC_{inf}$ in the range of 2,057 to 3,214 ng·hr/mL of N-(cyanomethyl)-4-(2-(4-morpholinophenylamino)pyrimidin-4-yl)benzamide.

52. The pharmaceutical composition of claim 51, wherein after a single oral administration said composition provides a pharmacokinetic profile substantially similar to that of a dosage form comprising N-(cyanomethyl)-4-(2-(4-morpholinophenylamino)pyrimidin-4-yl)benzamide dihydrochloride anhydrous Form I in an amount equivalent to 300 mg of free base N-(cyanomethyl)-4-(2-(4-morpholinophenylamino)pyrimidin-4-yl)benzamide.

53. A method for the treatment of a disease associated with Janus Kinase (JAK) which comprises administering to a subject in need thereof an effective amount of the pharmaceutical composition of claim 51, wherein the disease is a myeloproliferative disease selected from the group consisting of thrombocythemia, idiopathic myelofibrosis, systemic mastocystosis (SM), myelodysplastic syndrome (MDS) and systemic mast cell disease (SMCD).

54. A method for the treatment of a disease associated with Janus Kinase (JAK) which comprises administering to a subject in need thereof:

an effective amount of a therapeutic agent that inhibits or modulates the activity of a bromodomain-containing protein; and an effective amount of N-(cyanomethyl)-4-(2-(4-morpholinophenylamino) pyrimidin-4-yl)benzamide dihydrochloride monohydrate Form II.

55. The method of claim 54, wherein the therapeutic agent is a bromodomain-containing protein (BRD) inhibitor.

56. The method of claim 55, wherein the therapeutic agent is a BRD4 inhibitor.

57. The method of claim 54, wherein the N-(cyanomethyl)-4-(2-(4-morpholinophenylamino) pyrimidin-4-yl)benzamide dihydrochloride monohydrate Form II is crystalline.

58. The method of claim 54, wherein the N-(cyanomethyl)-4-(2-(4-morpholinophenylamino) pyrimidin-4-yl)benzamide dihydrochloride monohydrate Form II is crystalline and (a) the crystals have unit cell parameters at T=100° K of: a=10.2837(6) Å, b=10.4981(6) Å, c=11.5143(7) Å, α=83.297(2)°, β=87.649(2)°, y=67.445(2)°, and a triclinic P-1 space group;

(b) is characterized by an X-ray powder diffraction (XRPD) pattern substantially as set forth in FIG. 5;

(c) is characterized by a differential scanning calorimetry (DSC) pattern substantially as set forth in FIG. 8; or (d) is characterized by a dynamic vapor sorption (DVS) pattern substantially as set forth in FIG. 14.

59. The method of claim 54, wherein the disease is a myeloproliferative disease selected from the group consisting of thrombocythemia, idiopathic myelofibrosis, systemic mastocystosis (SM), myelodysplastic syndrome (MDS) and systemic mast cell disease (SMCD).

60. The method of claim 54, wherein the N-(cyanomethyl)-4-(2-(4-morpholinophenylamino) pyrimidin-4-yl)benzamide dihydrochloride monohydrate Form II is provided in a pharmaceutical composition that is in a solid form.

61. The method of claim 60, wherein N-(cyanomethyl)-4-(2-(4-morpholinophenylamino)pyrimidin-4-yl)benzamide dihydrochloride monohydrate Form II is present in an amount equivalent to 50 mg, 100 mg, 150 mg, or 200 mg of free base N-(cyanomethyl)-4-(2-(4-morpholinophenylamino)pyrimidin-4-yl)benzamide.

62. The method of claim 61, wherein N-(cyanomethyl)-4-(2-(4-morpholinophenylamino)pyrimidin-4-yl)benzamide dihydrochloride monohydrate Form II is in the form of a tablet.

* * * * *